US010830692B2

(12) United States Patent
Wang et al.

(10) Patent No.: US 10,830,692 B2
(45) Date of Patent: *Nov. 10, 2020

(54) SYSTEM AND METHOD TO MEASURE DISSOLVED GASES IN LIQUID

(71) Applicant: Woods Hole Oceanographic Institution, Woods Hole, MA (US)

(72) Inventors: Zhaohui 'Aleck' Wang, N. Falmouth, MA (US); Frederick N. Sonnichsen, Woods Hole, MA (US)

(73) Assignee: WOODS HOLE OCEANOGRAPHIC INSTITUTION, Woods Hole, MA (US)

(*) Notice: Subject to any disclaimer, the term of this patent is extended or adjusted under 35 U.S.C. 154(b) by 234 days.

This patent is subject to a terminal disclaimer.

(21) Appl. No.: 16/120,248

(22) Filed: Sep. 1, 2018

(65) Prior Publication Data

US 2019/0064062 A1    Feb. 28, 2019

Related U.S. Application Data

(63) Continuation-in-part of application No. 14/722,370, filed on May 27, 2015, now Pat. No. 10,067,111.
(Continued)

(51) Int. Cl.
*G01N 33/18* (2006.01)
*G01N 21/31* (2006.01)
(Continued)

(52) U.S. Cl.
CPC ............ *G01N 21/314* (2013.01); *G01N 1/38* (2013.01); *G01N 21/783* (2013.01); *G01N 33/18* (2013.01);
(Continued)

(58) Field of Classification Search
CPC .......... G01N 15/06; G01N 2015/0011; G01N 2015/0687; G01N 2015/0693;
(Continued)

(56) References Cited

U.S. PATENT DOCUMENTS 7,087,436 B2    8/2006   Baumgardner et al.
9,772,293 B2    9/2017   Nakano et al.
(Continued)

FOREIGN PATENT DOCUMENTS

WO    WO-2014-104128 A1    7/2014

OTHER PUBLICATIONS

Egleston, E. S. et al., Revelle revisited: Buffer factors that quantify the response of ocean chemistry to changes in DIC and alkalinity. Global Biogeochem. Cycles, 2010, pp. 1-9, vol. 24. GB1002, doi:10.1029/2008GB003407, Amer. Geophys. Union.
(Continued)

*Primary Examiner* — Maureen Wallenhorst
(74) *Attorney, Agent, or Firm* — Douglas Denninger; Gabriel Hendricks

(57) ABSTRACT

A high-resolution in situ sensing system and method for providing continuous measurements of at least one dissolved analyte including a sample processing cell having at least a first conduit defining a first passage with at least one selectively-permeable wall capable of passing a portion of the sample liquid into a processing, fluid. The at least one selectively-permeable wall substantially resists flow of another portion of the sample liquid therethrough. Processing fluid is directed through the first conduit while moving the sample liquid and the reagent fluid relative to each other in one of a stationary, concurrent or a countercurrent flow relationship to achieve either partial or full equilibration between the sample liquid and processing fluid to generate
(Continued)

at least partially equilibrated reagent fluid and a processed sample in a substantially continuous manner.

22 Claims, 19 Drawing Sheets

Related U.S. Application Data

(60) Provisional application No. 62/003,233, filed on May 27, 2014.

(51) Int. Cl.
| | |
|---|---|
| *G01N 21/05* | (2006.01) |
| *G01N 1/38* | (2006.01) |
| *G01N 31/22* | (2006.01) |
| *G01N 21/78* | (2006.01) |
| G01N 21/80 | (2006.01) |
| G01N 15/06 | (2006.01) |

(52) U.S. Cl.
CPC ..... *G01N 33/1886* (2013.01); *G01N 33/1893* (2013.01); *G01N 15/06* (2013.01); *G01N 21/05* (2013.01); *G01N 21/80* (2013.01); *G01N 31/221* (2013.01); *G01N 2201/0212* (2013.01); *G01N 2201/0216* (2013.01); *G01N 2201/0218* (2013.01); *Y10T 436/235* (2015.01); *Y10T 436/255* (2015.01)

(58) Field of Classification Search
CPC ...... G01N 21/05; G01N 21/31; G01N 21/314; G01N 21/78; G01N 21/783; G01N 21/80; G01N 31/221; G01N 33/18; G01N 33/1846; G01N 33/1886; G01N 33/1893; G01N 1/38; G01N 2201/0212; G01N 2201/0216; G01N 2201/0218; Y10T 436/117497; Y10T 436/175383; Y10T 436/176152; Y10T 436/20; Y10T 436/204998; Y10T 436/207497; Y10T 436/23; Y10T 436/235; Y10T 436/255; Y10T 436/2575
USPC ..... 436/52, 68, 73, 113, 114, 127, 133, 136, 436/145, 146, 163, 164, 165, 167, 168, 436/178, 180; 422/81, 82.05, 82.09, 535
See application file for complete search history.

(56) References Cited

U.S. PATENT DOCUMENTS

| | | | |
|---|---|---|---|
| 10,067,111 | B2 * | 9/2018 | Wang ..................... G01N 15/06 |
| 2015/0246314 | A1 | 9/2015 | Constantz et al. |

OTHER PUBLICATIONS

Fabry, V.J. et al., Impacts of ocean acidification on marine fauna and ecosystem processes. 2008, pp. 414-432, V. 65 (3) J. Mar. Sci., ICES.

Feely, R.A. et al., Ocean Acidification: Present Conditions and Future Changes in a High-CO2 World. 2009, pp. 36-47, V. 22(4), Oceanography.

Le Quere, C. et al., Impact of climate change and variability on the global oceanic sink of CO2, 2010, pp. 1-10, V. 24, Global Biogeochem. Cy. DOI: 10.1029/2009GB003599.

Li, Q.L. et al., Automated spectrophotometric analyzer for rapid single-point titration of seawater total alkalinity. 2013,pp. 11139-11146, V. 47 (19),Environ. Sci. Technol.

Liu, X.W. et al., Purification and characterization of meta-cresol purple for spectrophotometric seawater pH measurements, 2011, pp. 4862-4868, vol. 45 (11), Environ. Sci. Technol., Amer. Chem. Soc.

Liu,X.W. et al., Spectrophotometric measurements of pH in-situ: Laboratory and field evaluations of instrumental performance, 2006, pp. 5036-5044, vol. 40(16), Environ. Sci. Technol., Amer. Chem. Soc.

Martz, T.R. et al., Testing the Honeywell Durafet (R) for seawater pH applications, 2010, pp. 172-174, V.8, Limnol Oceanogr-Meth., Amer. Soc. Limn. Oceanogr.

Nakano, Y. et al., Simultaneous vertical measurements of in situ pH and CO2 in the sea using spectrophotometric profilers, 2006, pp. 71-81, V.62(1), J. Oceanogr.

Orr, J.C. et al., Anthropogenic ocean acidification over the twenty-first century and its impact on calcifying organisms, 2005, pp. 681-686, V. 437, Nature, Nature Publ. Group, Doi 10.1038/Nature04095.

Seidel, M.P. et al., A sensor for in situ indicator-based measurements of seawater pH,2008,pp. 18-28, V.109 (1-2), Mar. Chem. Doi 10.1016/j.marchem.2007.11.013.

Wang, Z.A. et al., High-frequency spectrophotometric measurements of total dissolved inorganic carbon in seawater, 2013, pp. 7840-7847, V.47, Environ. Sci. Technol.

Wanninkhof, R. et al., Global ocean carbon uptake: magnitude, variability and trends, 2013, pp. 1983-2000, V.10, Biogeosciences, Eur. Geos. U.

Yao, W.S. et al., Spectrophotometric determination of freshwater pH using bromocresol purple and phenol red, 2001, pp. 1197-1201, V.35(6), Environ. Sci. Technol., Amer. Chem. Soc.

Zhang, H.N. et al., Spectrophotometric pH measurements of surface seawater at in-situ conditions: Absorbance and protonation behavior of thymol blue, 1996, pp. 17-25, vol. 52, Mar. Chem., Elsevier Sci. B.V.

Callahan, M. et al., In-Situ Measurements of Cu in an Estuarine Environment Using a Portable Spectrophometric Analys System, Environ. Sci. Technol., 2004, pp. 587-593, vol. 38, No. 2, American Chem. Soc.

Barakat, M., New trends in removing heavy metals from industrial wastewater, Arabian J. Chem., 2011, pp. 361-377, vol. 4, Elsevier.

Wen, X. et al., Ultra-sensitive determination of cadmium in rice and water by UV-vis spectrophotometry after single drop microextraction, Spectrochimica Acta Part A: Molecular and Biomolecular Spectr., 2011, pp. 508-512, vol. 79, Elsevier.

Wen, X. et al., A new coupling of spectrophotometric determination with ultrasound-assisted emulsification dispersive liquid-liquid microextraction of trace silver, Spectrochimica Acta Part A: Molecular and Biomolecular Spectr., 2012, pp. 782-787, vol. 97, Elsevier.

Liu, X. et al., In Situ Spectrophotometric Measurement of Dissolved Inorganic Carbon in Seawater, Envir. Sci. Tech., 2013, pp. 11106-11114, vol. 47, ACS Publ.

Wang, Z. et al., Simultaneous spectrophotometric flow-through measurements of pH, carbon dioxide fugacity, and total inorganic carbon in seawater, Analytica Chimica Acta, 2007, pp. 23-36, vol. 596, Elsevier.

Wang, Z. et al., In Situ Sensor Technology for Simultaneous Spectrophotometric Measurements of Seawater Total Dissolved Inorganic Carbon and pH, Envir. Sci & Tech., 2015, pp. 4441-4449, vol. 49, ACS Publ, Elsevier.

* cited by examiner

SYSTEM AND METHOD TO MEASURE DISSOLVED GASES IN LIQUID

CROSS-REFERENCE TO RELATED APPLICATIONS

This application is a continuation-in-part of U.S. application Ser. No. 14/722,370 filed 27 May 2015, now U.S. Pat. No. 10,067,111 B2, which claims priority to Provisional Application No. 62/003,233 filed 27 May 2014. The entire contents of the above-mentioned applications are incorporated herein by reference.

STATEMENT REGARDING FEDERALLY SPONSORED RESEARCH

Federal funds awarded by the U.S. National Institute of Standards and Technology under Grant No. 60NANB10D024 and the U.S. National Science Foundation under Grant Nos. OCE-1041068 and OCE-1233654 contributed to making the invention. The U.S. Government has certain rights herein.

FIELD OF THE INVENTION

The invention relates to systems and methods of measuring dissolved analytes and more particularly to dynamic, real-time measurements within a liquid such as seawater.

CROSS-REFERENCE TO RELATED PUBLICATIONS

This application incorporates the entire contents of the following publications by reference: Wang et al., High-Frequency Spectrophotometric Measurements of Total Dissolved Inorganic Carbon in Seawater. Environ. Sci. Technol. 2013, 47: 7840-7847, and Wang et al., In Situ Sensor Technology for Simultaneous Spectrophotometric Measurement of Seawater Total Dissolved Inorganic Carbon and pH. Environ. Sci. Technol. 2015, 49: 4441-4449. The entire contents of the above-mentioned publications are incorporated herein by reference in their entirety.

BACKGROUND OF THE INVENTION

The marine carbon dioxide ($CO_2$) system plays a critical role in regulating $CO_2$ fluxes into and out of the world's oceans. One of the primary mechanisms by which the ocean affects the Earth's climate is through regulating $CO_2$ gas into and out of the ocean via the marine $CO_2$ system. Currently, the ocean absorbs about one third of the anthropogenic $CO_2$ released to the atmosphere by human activities, thus playing a major role in reducing the rate of atmospheric $CO_2$ increase and thereby curbing global warming. However, oceanic uptake of anthropogenic carbon is causing a rapid change in seawater carbonate chemistry, often referred to as ocean acidification, wherein excess $CO_2$ lowers seawater pH, increases total $CO_2$ concentration, and decreases calcium carbonate saturation. Changes in the marine $CO_2$ system may result in complicated responses and feedbacks in the ocean, ranging from changes in marine carbon and other elemental cycles to marine biology and ecology. Ocean acidification also reduces seawater buffering capacity, slowing down oceanic carbon uptake and acting as a positive feedback to the atmospheric $CO_2$ increase The four primary parameters used to characterize the marine $CO_2$ system are total dissolved inorganic carbon (DIC), partial pressure of $CO_2$ ($pCO_2$) or $CO_2$ fugacity ($fCO_2$), pH, and total alkalinity (TA). DIC is defined as the sum of all carbonic acid species in water: $DIC=CO_2^*+HCO_3^-+CO_3^{2-}$, where $CO_2^*$ is the sum of dissolved $CO_2$ and carbonic acid ($H2CO_3$). DIC is a master carbon parameter frequently used to study, identify, and differentiate many processes linked to the marine carbon cycle (e.g. biological uptake of $CO_2$, ocean acidification, and anthropogenic $CO_2$ penetration in the ocean). The assessment of these processes ultimately relies on high-quality measurements of seawater DIC. In addition, to fully characterize the $CO_2$ system through thermodynamic calculations, at least two $CO_2$ parameters must be measured. $CO_2$ calculations made using DIC data as one of the parameters yield results that are often more consistent with measured values. Because of its important role in the $CO_2$ system, DIC was measured during all of the major ocean carbon expeditions, such as the Climate Variability and Predictability (CLIVAR) Hydrography Program and the Joint Global Ocean Flux Study (JGOFS).

Theoretically, measurements of any two of the four parameters along with salinity and temperature can be used to calculate the other parameters and fully resolve carbonate chemistry using seawater acid-base equilibria. However, selection of different measurement pairs in practice will generate a range of calculation errors resulting from analytical errors, uncertainties in equilibrium constants, and their non-linear propagation in calculation. Using DIC or TA as one of the measured pair produces relatively small calculation errors, while selection of the $pCO_2$-pH pair for measurements causes large calculation bias even under the best analytical practice. Only in situ $pCO_2$ and pH measurements have become increasingly common in recent years on various platforms, such as buoys and profilers, as commercial $pCO_2$ and pH sensors are available. In contrast, in situ sensing for DIC and TA are much less mature, and are mostly under different development stages. Simultaneous, in situ measurements of two $CO_2$ system parameters with either DIC or TA as one of the two are highly desirable but extremely rare.

Traditional bottle sampling and subsequent analysis of DIC can only achieve limited spatiotemporal coverage mainly because of associated high costs and low throughput. Development of methodologies that are suitable for high-resolution in situ measurements of $CO_2$ parameters have been widely recognized as a research priority in the carbon and ocean acidification research community. Among various methods (e.g. coulometry, potentiometry, non-dispersive infrared (NDIR) method, and conductimetry) developed for high-precision DIC measurements, the spectrophotometric method offers high sensitivity, good stability, and direct measurements of water-phase samples. It can be 'calibration-free' in theory, thus reducing maintenance requirements. These attributes make it well suited for in situ underwater applications.

The existing spectrophotometric DIC method is based on spectrophotometric pH measurements where observed absorbances of a sulfonephthalein processing liquid, also referred to herein as a processing solution, an indicator solution, or an indicator, and its equilibrium properties are used to quantify sample pH. A piece of Teflon AF 2400 (DuPont™ copolymer) capillary tubing is used as both an optical cell and a $CO_2$ equilibrator as it is highly permeable to $CO_2$ molecules and can act as a liquid-core waveguide (LCW) for optical detection. The spectrophotometric detection occurs after full $CO_2$ equilibration is established between the pretreated sample and the processing solution across the Teflon AF tubing. In other words, the tubing is the same device for the sample processing and detecting. In such a system, the detection occurs down the length of the LCW, meaning a single measurement will read indicator at different amounts of equilibrium, down the length of the LCW. The indicator solution is motionless during the equilibration process. This method is similar in principle to the spectrophotometric $fCO_2$ method, but the sample is not pretreated (e.g. acidified) and a different indicator is used. Because the indicator does not directly mix with the sample in either of these methods, no dilution or perturbation to the seawater sample occurs.

The response time (i.e. the time required to obtain a stable reading for detection) of the existing spectrophotometric method is about 5 minutes, which is the $CO_2$ exchange time required to reach full $CO_2$ equilibration. This method has been used for underway measurements of flow-through seawater, and actual measurements are intermittent. Such a response is sufficient for some stationary measurements, such as bottle samples and buoy deployments, where discontinuous measurements are acceptable. However, it is not ideal for high-resolution measurements made on mobile platforms, particularly those such as Automated Underwater Vehicles (AUVs), Remotely Operated Vehicles (ROVs), gliders, or water-column profilers. At the 5-minute sampling interval, the spatiotemporal resolution on these mobile platforms may be limited for studying rapid changes on a scale down to minutes or meters and fine-scale features such as those encountered in coastal oceans and water-column profiling.

SUMMARY OF THE INVENTION

This invention features systems and methods that rapidly and at least substantially continuously measure at least one pre-selected dissolved analyte, often a dissolved gas, such as dissolved carbon dioxide, within a sample liquid such as freshwater or seawater obtained from a quantity of the liquid such as a pond, lake, stream, bay, or ocean. The system and method include selecting a sample processing cell having at least a first conduit defining a first passage with at least one analyte-permeable wall capable of passing at least the pre-selected dissolved analyte from the sample liquid into a reagent fluid. The at least one analyte-permeable wall substantially resists flow of the sample liquid therethrough, that is, it maintains liquid separation between the sample and reagent fluids. The system and method further include directing reagent fluid through the first conduit while moving the sample liquid and the reagent fluid relative to each other in one of a concurrent and a countercurrent flow relationship to achieve either partial or full equilibration between the sample liquid and reagent fluid to generate at least partially equilibrated reagent fluid in a substantially continuous manner. The quantity of the dissolved analyte in the at least partially equilibrated reagent is measured by spectrophotometry (using a processing solution as the reagent) or other measurement techniques. The sample liquid is obtained at least substantially continuously from the quantity of the liquid, preferably while the sample processing cell is immersed in the quantity of liquid. Measurement systems according to the present invention are suitable for installation and use in situ on Autonomous Underwater Vehicles (AUVs), Remotely Operated Vehicles (ROVs), gliders, profilers, and other mobile or stationary platforms, preferably to perform sampling and measurements at depths of at least 3,000 m or greater.

The term "reagent" as utilized herein refers to a processing fluid (e.g. an indicator fluid) or solution, preferably a liquid for submersible applications, for conducting spectrophotometric sensor measurements and refers to other types of fluids for conducting other types of sensor measurements. In some constructions, the processing solution is a pH indicator employed to produce a colorimetric change or other detectable chemical reaction in the presence of shift in other signals. Examples of other processing solutions include complexometric indicators (ionochromic dyes) that undergo chemical bonding (e.g. ionic complexes) with specific metal ions and redox indicators that undergo changes in oxidation state, both are often accompanied by color changes.

This invention also features an in situ sensing system, referred to herein as Channelized Optical System (CHANOS) or Dual-channel Modularized Autonomous System (D-MAS), that is capable of making high-resolution, simultaneous measurements of at least two parameters such as total dissolved inorganic carbon (DIC) and pH in seawater. Measurements made by this single, compact sensor can fully characterize the marine carbonate system. The system preferably has a modular design to accommodate two independent, but similar measurement channels for DIC and pH. Both are based on spectrophotometric detection of hydrogen ion concentrations. The pH channel preferably uses a flow-through, sample-processing solution mixing design to achieve near instantaneous measurements. The DIC channel utilizes the spectrophotometric method described herein to achieve flow-through $CO_2$ equilibration between a pretreated sample and a processing solution with a response time of only ~90 s. During laboratory and in situ testing, CHANOS achieved a precision of ±0.0010 and ±2.5 µmol $kg^{-1}$ for pH and DIC, respectively. In-situ comparison tests indicated that the accuracies of the pH and DIC channels over a three-week time-series deployment were ±0.0024 and ±4.1 µmol $kg^{-1}$, respectively. CHANOS can make in-situ, climatology-quality measurements by measuring two desirable $CO_2$ parameters, and is capable of resolving the $CO_2$ system in dynamic marine environments.

The CHANOS sensor is among the first that is able to fully resolve carbonate chemistry with a single system and a desirable pair of $CO_2$ system parameters measured to achieve small calculation errors. The CHANOS preferably has a build-in mechanism for in situ calibration, which ensures high measurement quality throughout a deployment and reduces the need for laboratory calibration. Preferably, the system is able to make high-resolution, climatology-quality measurements to resolve seawater-$CO_2$ system dynamics.

This invention further features a new spectrophotometric DIC method capable of attaining a much faster response time (approximately 70 seconds for full equilibrium and approximately 22 seconds for 60%-70% partial equilibrium in one embodiment wherein processing fluid has a transit time of approximately 10 seconds) using flow-through (dynamic) $CO_2$ equilibration by introducing countercurrent, continuous flow between the processing solution and the sample, as described below for FIGS. 1B and 2A. This embodiment allows for continuous measurements as compared to intermittent measurements made with the existing intermittent spectrophotometric method. The present method has achieved good measurement stability and repeatability, similar to those of the intermittent method. During field tests, the continuous method of the present invention produced high-resolution DIC data that were in good agreement with measurements made by the established Non-dispersive Infrared (NDIR)-based method. These characteristics make the continuous method particularly suitable for expanding observational capabilities of the $CO_2$ system on mobile observing platforms.

BRIEF DESCRIPTION OF THE DRAWINGS

In what follows, preferred embodiments of the invention are explained in more detail with reference to the drawings, in which.

DETAILED DESCRIPTION OF PRESENTLY PREFERRED EMBODIMENTS

Figure 1A:
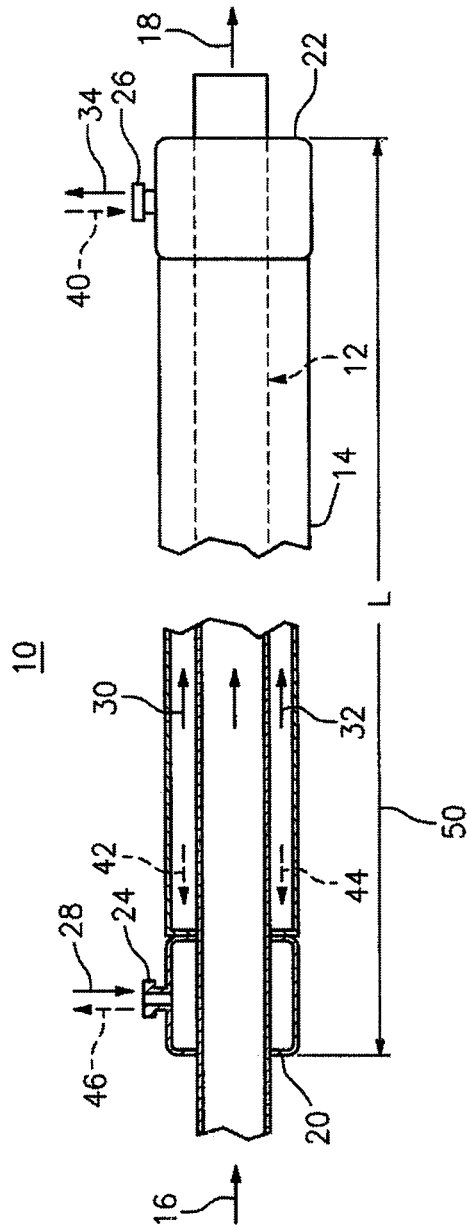
FIG. 1A is a schematic, partial cross-sectional view of a sample processing cell utilized according to the present invention for either concurrent or countercurrent flow of sample fluid relative to a reagent fluid.

This invention may be accomplished by systems and methods that rapidly and at least substantially continuously measure at least one pre-selected analyte, such as dissolved carbon dioxide or any suitable measurable substance which provides a colorimetric or detectable chemical change dependent on substance concentration or suitable analyte utilizing a equilibrium between analyte and liquid (e.g., carbon dioxide or ammonia), within a sample liquid such as freshwater or seawater obtained from a quantity of the liquid such as a pond, lake, stream, bay, or ocean. The system and method include selecting a sample processing cell appropriate for the pre-selected analyte. In the currently preferred embodiment, the sample processing cell has at least a first conduit defining a first passage with at least one selectively-permeable wall (e.g., membrane) capable of passing at least the pre-selected dissolved analyte from the sample liquid into a reagent fluid. In the preferred embodiments in which the analyte is a dissolved gas, the at least one analyte-permeable wall substantially resists flow of the sample liquid therethrough, that is, it maintains liquid separation between the sample and reagent fluids. In other embodiments, the permeable wall selectively allows passage of specific substances (e.g. dissolved metals or metal ions), while resisting the flow the sample liquid and other substances therein. The system and method further include directing reagent fluid through the first conduit while moving the sample liquid and the reagent fluid relative to each other in one of a concurrent and a countercurrent flow relationship to achieve either partial (e.g., at least 10%, at least 20%, at least 30%, at least 40%, or more preferably at least 50% equilibrium) or full 100% equilibration between the sample liquid and reagent fluid to generate at least partially equilibrated reagent fluid in a substantially continuous manner. The quantity of the analyte in the at least partially equilibrated reagent fluid is measured by spectrophotometry or other measurement techniques. The sample liquid is obtained at least substantially continuously from the quantity of the sample liquid while the sample processing cell is immersed in the quantity of sample liquid (either directly or via a chamber or housing filled with seawater, fresh water, oil, etc.). Measurement systems according to the present invention are suitable for installation and use in situ on AUVs, ROVs, gliders, profilers, and other mobile or stationary platforms for submerged or water surface deployments. Other embodiments of the inventive system are adapted for land in wet or dry conditions such as in a laboratory setting.

In certain constructions, the system and method include at least a second measurement channel to measure another parameter such as pH, alkalinity or a substance's concentration. Other parameters may include total alkalinity (TA), partial pressure of $CO_2$, ammonia, heavy metals, or other suitable substances. Examples are provided below for an in situ (i.e., in the location of sample acquisition) DIC-pH sensor, Channelized Optical System (CHANOS), also referred to as a Dual-channel Modularized Autonomous System (D-MAS), for spectrophotometric DIC and pH measurements according to another embodiment of the present invention. Measurements according to the present invention preferably are conducted substantially in "real time", that is, with minimal response time (preferably less than one minute for countercurrent flow, more preferably less than 30 seconds, most preferably less than 15 seconds, and truly continuously for concurrent flow with a time lag of less than five minutes) in obtaining meaningful readings of the target parameter, even in deep ocean, high-pressure conditions. Other than optionally pretreating the sampled water, such as with an acid or base to convert a targeted substance (e.g. a carbonate species) to a second target substance (i.e. converting a dissolved substance to a gaseous substance), no poisoning, preserving or stabilizing of the samples is needed. In other embodiments, the sampled water is treated (either pretreated or post-treated) with one or more reagents for such purposes as preserving, treating, or otherwise altering the sample prior to or after measurement.

Sample Processing Cell

In the preferred embodiment a sample processing cell 10, FIG. 1A, includes a first conduit 12, having at least one selectively-permeable wall, within a second, surrounding conduit 14. In this construction, reagent fluid is introduced to one end of cylindrical first conduit 12, as indicated by arrow 16, and exits from the other end of conduit 12 as indicated by arrow 18. A second, preferably concentric, conduit 14 is bounded by connectors 20 and 22 defining openings 24 and 26, respectively.

For concurrent flow relative to flow arrows 16 and 18 of the reagent fluid, sample liquid is introduced through opening 24, as indicated by arrow 28, travels along the exterior of first conduit 12 as indicated by flow arrows 30 and 32, and exits through opening 26 as indicated by arrow 34. For countercurrent flow, sample liquid is introduced through opening 26, dashed arrow 40, flows along first conduit 12 as indicated by dashed arrows 42 and 44, and exits through opening 24 as indicated by dashed arrow 46. Sample processing cell 10 has an effective transfer length L, indicated by arrow 50, representing the length over which dissolved analyte equilibrates, that is, the analyte is transferred at least partially, from the sample liquid to the reagent fluid.

In one embodiment, as described by Z. A. Wang, S. N. Chu, and K. A. Hoering in "High-Frequency Spectrophotometric Measurements of Total Dissolved Inorganic Carbon in Seawater", *Environ. Sci. Technol.* 2013, 47 (14), 7840-7847 and shown in FIGS. 1B and 2A of parent application Ser. No. 14/722,370, now U.S. Pat. No. 10,067,111 B2, the spectrophotometric system and method according to the present invention achieve substantially continuous measurements of total dissolved inorganic carbon (DIC) in seawater. It uses a countercurrent flow design and a highly $CO_2$-permeable membrane (Teflon AF 2400) to achieve flow-through $CO_2$ equilibration between an pretreated sample and an processing solution (e.g. an indicator) with a fast response time of approximately 70 seconds for full equilibrium and approximately 22 seconds for 60%-70% partial equilibrium in one embodiment wherein processing fluid has a transit time of approximately 10 seconds. The processing fluid, described in more detail below, is defined for the purposes of this disclosure as any fluid or liquid that aids or enables the measurement of at least one desired analyte. In some cases the processing fluid comprises a dye, indicator, or a solution that changes color or the wavelength of absorption when it reacts (binds or interacts with) to an analyte. The processing fluid may also transition from a clear, non-absorbing fluid to one of color, or fluorescence. In some embodiments, the processing fluid does not contain an indicator, but other chemicals or properties that induce measurement. In some embodiments, the analyte is directly measured and the processing fluid is utilized to transition or transfer the analyte into the best conditions for measurement (e.g. pH, buffered salt solution or the like). This method improves the spatiotemporal resolution by more than one order of magnitude compared to the existing spectrophotometric method. The flow-through equilibration allows for continuous (~1 Hz) detection and real-time data smoothing. The method had a short-term precision of ±2.0 µmol kg$^{-1}$ for a given flow-through sample. It achieved a field precision of ±3.6 µmol kg$^{-1}$ and successfully captured high DIC variability down to minute scales. Measurements by the new method over the typical range of oceanic DIC showed good agreement with measurements made by an established method (mean differences −1.6-0.3 µmol kg$^{-1}$ with 1σ±6.0-6.7 µmol kg$^{-1}$). This level of precision and accuracy is comparable to that of the existing spectrophotometric method. The characteristics of the new method make it particularly suitable for high-frequency, submerged (e.g., partially or fully submerged) measurements required for mobile observing platforms in the ocean. It can also be adapted for high-frequency, spectrophotometric measurements of seawater $CO_2$ fugacity.

Figure 1B:
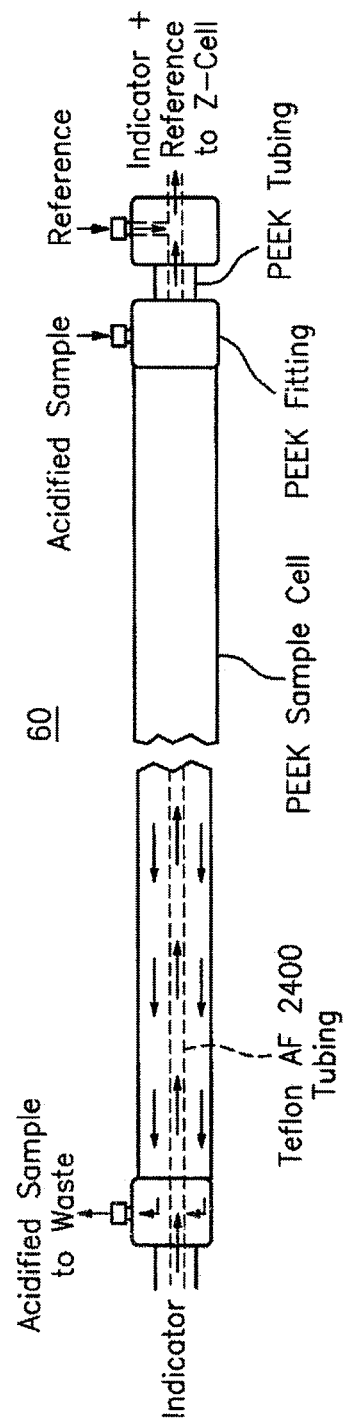
FIG. 1B is a schematic, partial cross-sectional view of a sample processing cell utilized according to the present invention for countercurrent flow utilizing Teflon AF tubing.

Described herein is a new spectrophotometric DIC method capable of attaining a much faster response time (e.g., about 22 s or less, less than 30 s, less than 1 min) using flow-through (dynamic) $CO_2$ equilibration by introducing countercurrent, continuous flow between the processing solution and the liquid undergoing analysis, also referred to as the "sample", within sample processing cell 60, FIG. 1B. This new design allows for continuous measurements as compared to intermittent measurements made with the known, existing spectrophotometric method (referred to as the "intermittent method" hereafter). The new method according to the present invention (also referred to as the "continuous method" or "present method" hereafter) has achieved good measurement stability and repeatability, similar to those of the intermittent method.

During field tests, the continuous method produced high temporal resolution DIC data that were in good agreement with measurements made by the established NDIR-based method. These characteristics make the continuous method particularly suitable for expanding observational capabilities of the $CO_2$ system on mobile observing platforms.

The intermittent spectrophotometric DIC method relies on 100% $fCO_2$ equilibration between pretreated samples and a motionless processing solution across the wall of Teflon AF tubing. After $fCO_2$ equilibrium, DIC (as total $CO_2$) of the pretreated sample (denoted by subscript a) is proportional to $fCO_2$ of the internal processing solution (denoted by subscript i):

$$\log(fCO_2)_a = \log\frac{[DIC]}{(K_0)_a} = \log(fCO_2)_i \qquad (1)$$

where $(K_0)_a$ is the Henry's Law constant for the pretreated (e.g. acidified) sample. The chemical and optical properties of the internal processing solution can be expressed as:

$$\log(fCO_2)_i = B(t) - \log(K_0)_i - \log\left(\frac{R - e_1}{1 - Re_3/e_2}\right) \qquad (2)$$

such that:

$$\log\frac{[DIC]}{(K_0)_a} = B(t) - \log(K_0)_i - \log\left(\frac{R - e_1}{1 - Re_3/e_2}\right) \qquad (3)$$

$(K_0)_i$ is the Henry's Law constant for the internal processing solution. The coefficients $e_1$, $e2$, and $e_3$ are processing solution molar absorbance ratios at wavelengths $\lambda_1$ and $\lambda_2$, where $\lambda_1$ and $\lambda_2$ are the wavelengths for the absorbance maxima of the processing acid (HI$^-$) and base (I$^{2-}$) species. These coefficients are laboratory determined optical constants. R is the ratio of the processing solution absorbance (A) measured at wavelengths $\lambda_1$ and $\lambda_2$, $R = _{\lambda_2}A_{\lambda_1}$. B(t) can be expressed as:

$$B(t) = \log(TA + [H^+] - [I^{2-}])_i + \log\left(\frac{K_I e_2}{K_1'}\right)_i \qquad (4)$$

where TA is the alkalinity of the processing solution; [H$^+$] is the internal proton concentration; $K_1$ is the processing solution dissociation constant; and $K_1'$ is the carbonic acid first dissociation constant for the internal solution. B(t) describes the chemical and optical properties of the processing solution. It is an experimentally derived constant for a given temperature, calibrated using Certified Reference Material (CRM) obtained from A.G. Dickson at Scripps Institution of Oceanography.

For this work, Equation 3 has been re-arranged from the expression in the intermittent method by combining $(K_0)_a$ with the DIC concentration such that all sample-related terms are on one side of the equation, while all processing solution-related terms are on the other. Bromocresol purple was used as the pH indicator, where $\lambda_1$=432 nm and $\lambda_2$=589 nm. A non-absorbing reference wavelength ($\lambda_{ref}$=700 nm) was used to correct baseline drift in absorbance measurements. The governing equations or values for all of the constants and coefficients in Equations 1-4 were previously described by Byrne and colleagues. Equation 3 quantitatively links DIC and fCO$_2$ in the pretreated (e.g. acidified) sample to fCO$_2$ and pH of the internal processing solution at full CO$_2$ equilibration.

To make high-frequency DIC measurements possible, the new continuous DIC method uses a dynamic, partial equilibration process instead of a static, full equilibration which occurs in the intermittent method. A countercurrent flow design 60, FIG. 1B, was adopted to maintain fast and stable CO$_2$ exchange between the processing solution and pretreated sample. Countercurrent flow has been found extensively throughout nature in biological systems, such as in lungs and fish gills and has been imitated in engineering applications to achieve the maximum transfer of heat or chemicals. In this case, it maximizes the transfer rate of CO$_2$ between the processing solution and samples.

In the continuous method, the Teflon AF tubing can be utilized as either only an analyte equilibrator or as both an equilibrator and detector. In the presently preferred embodiment, the Teflon AF tubing was used only as a CO$_2$ equilibrator, not as both an equilibrator and a LCW as in the intermittent method. A system that uses the sample processing cell as both an equilibrator and a LCW detects processing solution at a range of equilibrium states with the sample water. The instant invention provides several methods to measure a discrete, homogenous sample at a single equilibrium state. The currently preferred CHANOS embodiment provides a separate sample processing cell and a detector. In other embodiments, the detector measures at one or more spots along the sample processing cell, each with a homogenous equilibrium states. For example, the second conduit has at least a single analyte-permeable wall on one plane (e.g. horizontal) and two measurement windows across from each other in two walls in another plane (e.g. vertical walls), perpendicular to the flow, allowing for measurement at a discrete, equilibrium homogenous sample site.

Other membranes or tubing may be used including silicone, bioabsorbable polymers or other suitable materials allowing high analyte and low liquid permeability. As described in more detail below in relation to FIG. 2, in the presently preferred embodiment, optical detection occurs in an measurement 'Z' cell after the processing solution passes through the Teflon AF tubing of FIG. 1B. As the processing solution travels the length of the Teflon AF tubing, partial CO$_2$ equilibration is attained between the processing solution and the pretreated sample. For a given sample, if such an equilibration process is repeatable each time the processing solution passes through the Teflon tubing, and the detection is stable and sensitive, then the method can achieve continuous, high-quality DIC measurements. If desired, a slow processing solution flow rate, combined with a long piece of Teflon AF tubing, will allow the processing solution to reach 100% CO$_2$ equilibration.

The countercurrent flow design allows for dynamic, efficient exchange of CO$_2$ across the permeable tubing. If the processing solution flows at a fast speed, by the time it reaches the end of the flow cell it has attained partial CO$_2$ equilibration with an exchange efficiency or percentage of equilibration, p (value 0-1), which can be included in Equation 3 to describe the continuous method:

$$\log\left(p \times \frac{[DIC]}{(K_0)_a}\right) = B(t) - \log(K_0)_i - \log\left(\frac{R - e_1}{1 - Re_3/e_2}\right), \qquad (5)$$

where $$\log(p \times fCO_2)_a = \log\left(p \times \frac{[DIC]}{(K_0)_a}\right).$$

In Equation 5, the right side still represents (fCO$_2$)$_i$ while p is added to the left side of the equation to characterize partial fCO$_2$ equilibration. The variable p is used to characterize the equilibration process and is affected by operational conditions such as flow rate, temperature, processing solution composition, and the fCO$_2$ gradient between the internal processing solution and the external sample. It can be empirically built into the calibration and does not need to be explicitly defined for actual measurements. When p=1, Equations 3 and 5 are equivalent.

Processing Solution

The processing is any fluid that enables the measurement of the desired analyte. In some cases, the processing fluid comprises a dye, indicator, or a solution that changes color or the wavelength of absorption when it reacts (binds or interacts with) to an analyte. The processing fluid may also transition from a clear, non-absorbing fluid to one of color, or fluorescence. In some embodiments, the processing fluid does not contain an indicator, but other chemicals or properties that induce measurement. In some embodiments, the analyte is directly measured and the processing fluid is utilized to transition or transfer the analyte into the best conditions for measurement (e.g. pH, buffered salt solution or the like). In the preferred CHANOS embodiment, the processing solution is adapted to accept the desired analyte ($CO_2$) across the analyte-permeable membrane and aid in its measurement, by further comprising an indicator (e.g. bromocresol purple).

CHANOS Analyte Channel

Figure 2A:
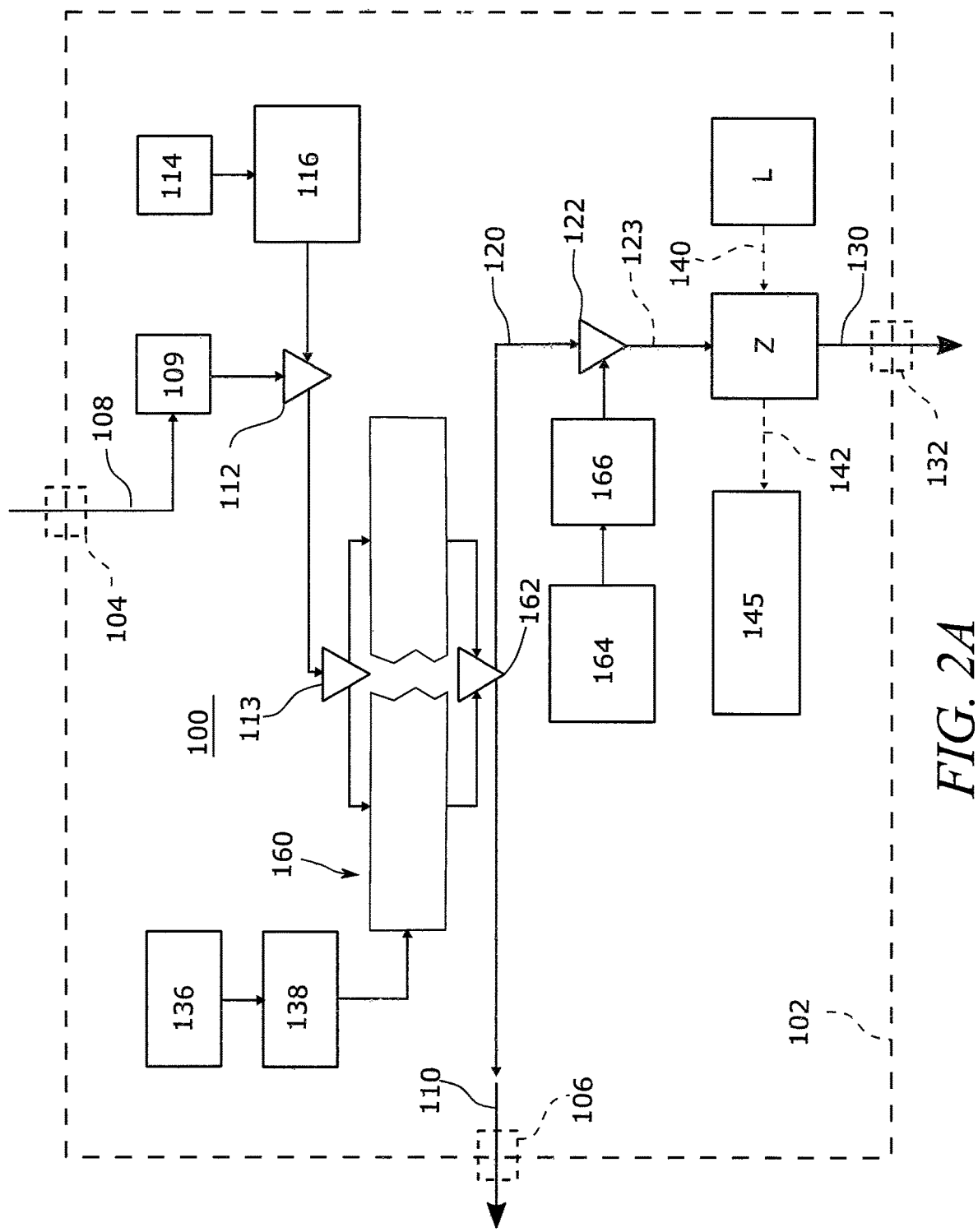
FIG. 2A is a schematic block diagram of a system according to the present invention utilizing countercurrent flow.

System 100 according to one embodiment of the present invention, FIG. 2A, is submersible in some constructions and, in other constructions, has one or more components that are not submersible. For submersible constructions, system 100 preferably is located within at least one water-tight housing 102 having ports 104 and 106, all depicted in dashed lines, for sample liquid intake, arrow 108, and sample outflow, arrow 110, respectively. Sample liquid intake 108 is configured to introduce a portion of the sample from the environment to the system. Similarly, sample outflow 110 is configured to remove the sample liquid from the system. Some embodiments will further preserve a portion of the outflowing sample in a preservation mechanism. The preservation mechanism may comprise any sampling system as known in the art, for example a bottle sampler, or a SUPR sampler. The preservation may be done before or after processing or measuring, and comprises a reservoir connected to a valve originating from lines 108, 120, 123 or 130.

Figure 17:
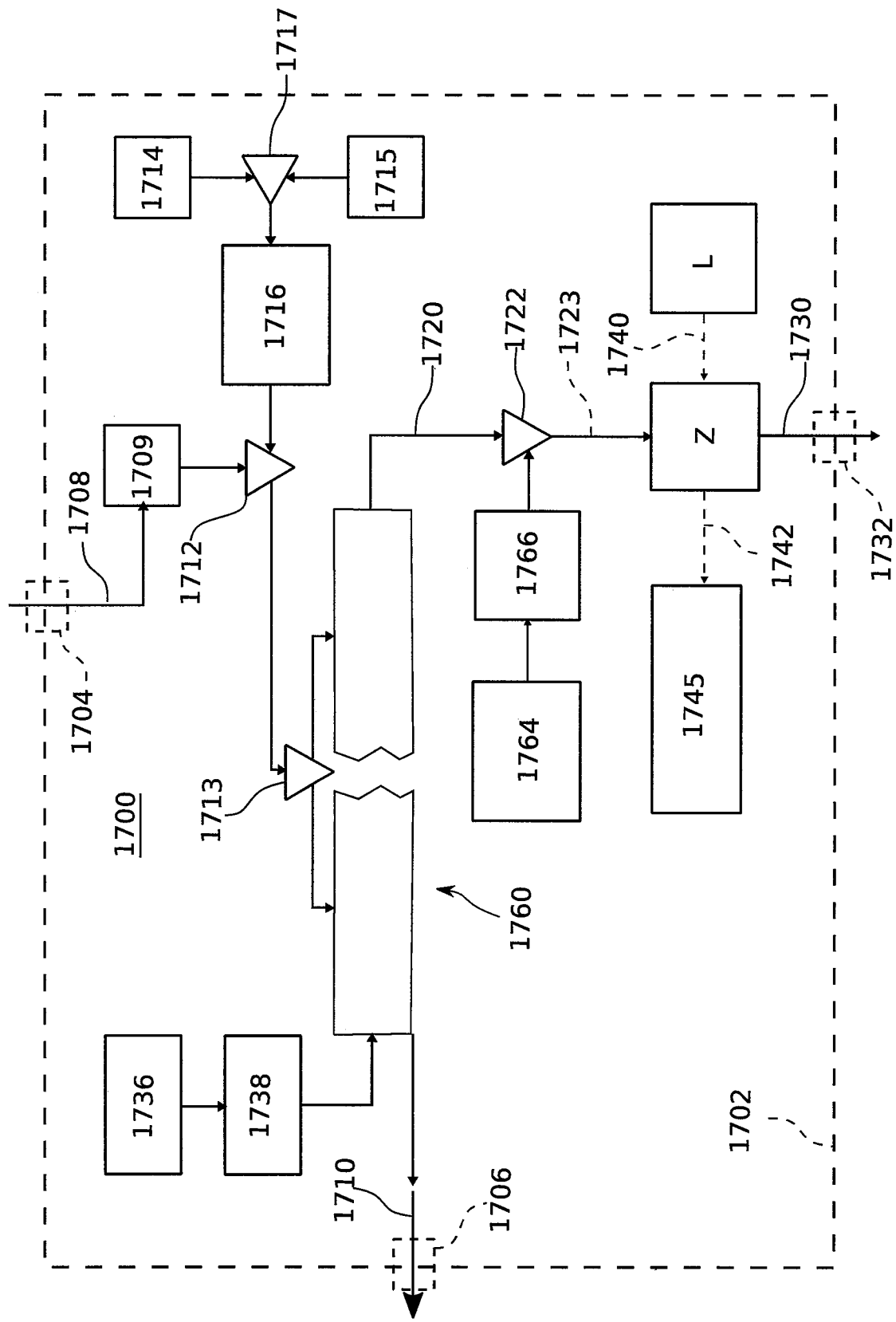
FIG. 17 is a schematic block diagram of a MENTOS channel according to the present invention.

Certain control mechanism such as valves and pumps preferably are contained in one or more oil-filled chambers to minimize the effects of changes in ambient pressure while maintaining separation from potentially corrosive sample liquids such as seawater, as will be familiar to those skilled in submersible technologies. In some embodiments, an oil such as a hydraulic oil (e.g., Royal Purple #7), a mineral oil, a synthetic oil, a composition of oils or other pressure-resistant fluid which comprises a compressibility of less than 10%, preferably less than 5%, and more preferably less than 1% per thousand meters water is used to fill the chambers within the system. The sample liquid 108, such as seawater, is drawn in by sample pump 109 and is mixed at a valve 112 (e.g., T-type valve) with pretreatment solution (e.g. acid) delivered from pretreat mechanism 114 via pretreatment pump 116. In this construction, the pretreated sample is then passed through a directional mechanism, also referred to as the director, before entering the processing cell. The director 1713, allows for a single embodiment to move sample in a countercurrent or concurrent relationship to processing liquid. In some embodiments, the director is incorporated into the valve 112, itself having output options for concurrent and countercurrent flow. In other embodiments, the director is a separate valve 1713, as depicted in FIG. 17, often a T-type valve. A sample processing cell 60' in a countercurrent relationship to processing liquid delivered from processing reservoir 136 via processing pump 138 is illustrated in FIG. 1A. Countercurrent flow cell 60' is similar to concurrent sample processing cell 60, FIG. 1B.

Pretreatment Mechanism

The optional pretreatment mechanism allows for the sample liquid to be altered, or otherwise optimized before entering the processing cell. In the CHANOS embodiment described herein, the pretreatment mechanism comprises an acid reservoir and a pump to mix sample and acid together. The reservoir contains a substantial amount of acid, preferably concentrated, that can be diluted with the sample via the pump to pretreat the sample. In many embodiments, the pretreatment (e.g., acidification) drives a chemical reaction, reacting with the analyte and producing a product suitable for measurement. In the CHANOS embodiment, pretreatment drives the analyte into the gaseous phase, allowing equilibration across the membrane in the sample processing cell. In other embodiments, the pretreatment mechanism contains a reservoir filled with a basic solution (e.g., NaOH), such that the sample is alkalified prior to entering the sample processing cell.

In other embodiments, the pretreatment mechanism enables chemical pre-treatment, such as coagulants or polymers used to precipitate analytes for collection, or for the removal of non-analytes. In further embodiments, the sample is pretreated with a gas, for example pure Nitrogen gas ($N_2$) to strip out unwanted nitrogen-containing species when the analyte is dissolved organic nitrogen, or a similar analyte, as describe in Wang et al., Toxicological & Environmental Chemistry, p. 679-688, 2016 and incorporated by reference herein. Embodiments described herein may also incorporate multiple pretreatment mechanism. Multiple reservoirs can be incorporated into one channel and each be added to the sample before or during the sample's entry to the processing cell. Other, known pretreatments are allowable in this system with the pretreatment mechanism.

After the processing liquid is exposed to the pre-selected analyte in the sample stream within cell 60', the at least partially equilibrated processing liquid 120 is directed through an measurement cell Z and exits as waste stream 130, through port 132, for disposal. System 100 preferably includes a reference fluid for calibration of the measuring sensor or instrument such as a spectrophotometer 145. In one construction, fluid delivery to cell Z is alternated by a T-type valve 122 (or other multiport flow controlled entry) between the equilibrated processing liquid 120 and a reference liquid from reference reservoir 164 via reference pump 166 for baseline measurements before and/or after processing solution measurements. In another construction, reference liquid is delivered directly to cell Z as indicated by dashed line 123, and valve 122 is a simple flow control valve solely for the at least partially equilibrated processing liquid 120.

Measurement

Measurement of the pre-selected analyte is accomplice at measurement cell Z. The present invention provides a means to deliver any type of electromagnetic energy from source L to measurement cell Z, for measurement by device 145. Measurement may be conducted by any means as known in the art, including optical, sound, magnetic, electrical, or electrochemical. In the preferred embodiment, optical radiation is delivered from source L to measurement cell Z via source guide 140 (e.g. a fiber optic cable or other waveguide). After the optical radiation passes through the processing solution or reference liquid in measurement cell Z, it is directed to a spectrophotometer 145 via a guide 142 (e.g. fiber optic cable or other waveguide). Power to operate the pumps, lamp and spectrophotometer units can be obtained from the platform which carries system 100, from a separate battery pack within system 100, or from batteries within the individual units themselves. One or more controllers (not shown) are provided to control the operation of the pumps and valves.

Additional Measurement Configurations

Figure 2B:
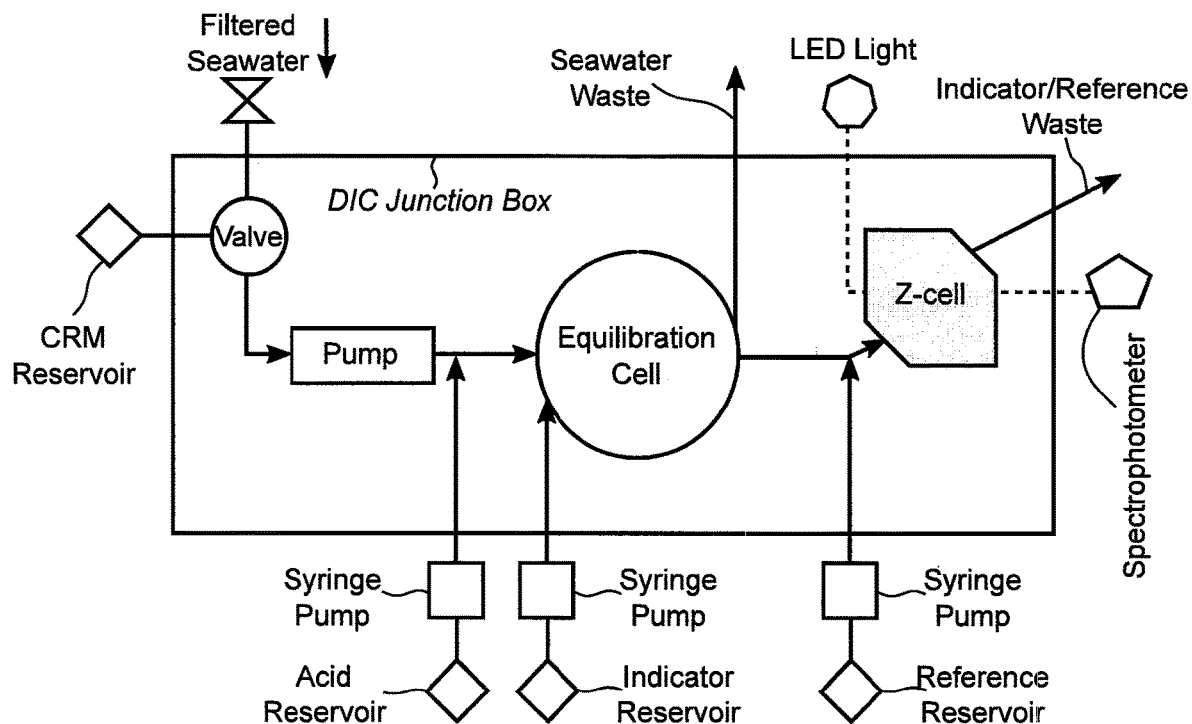
FIG. 2B is a schematic block diagram of a DIC channel of an in situ DIC-pH sensor system of FIG. 2D, referred to herein as a Channelized Optical System (CHANOS) or Dual-channel Modularized Autonomous System (D-MAS), for spectrophotometric DIC and pH measurements according to another embodiment of the present invention.
Figure 2C:
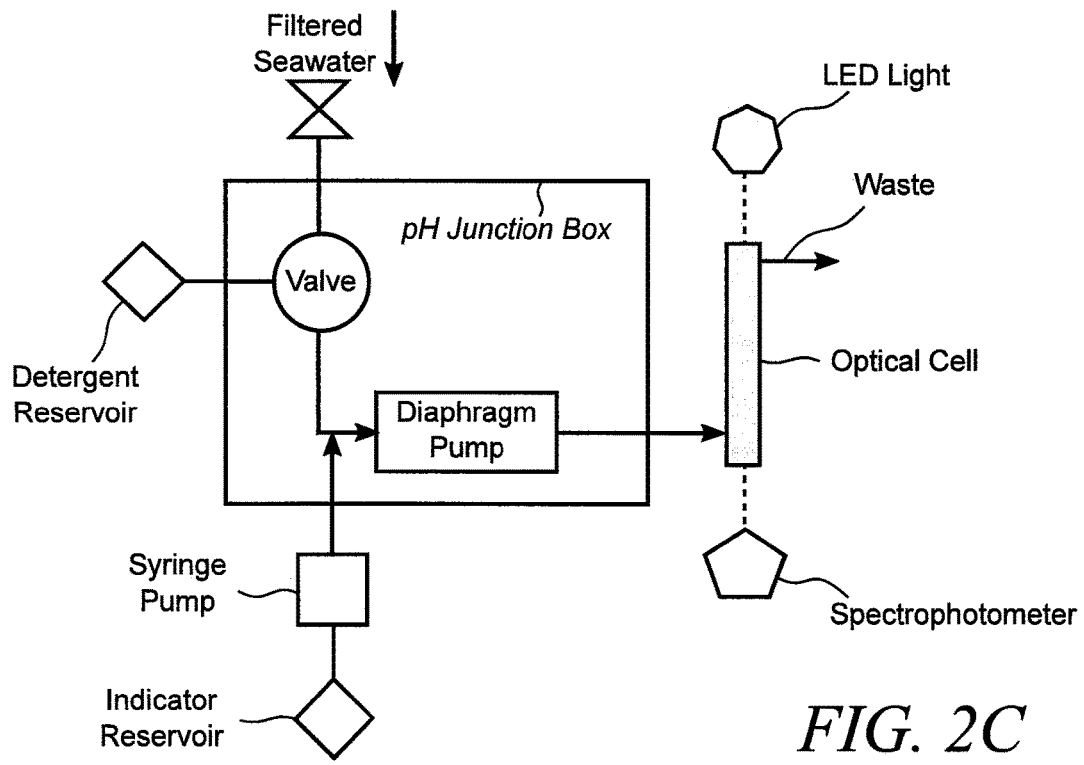
FIG. 2C is a schematic block diagram of a pH channel of the in situ DIC-pH sensor, dual-channel system of FIG. 2D.

The currently preferred CHANOS embodiment provides separate components for sample processing and measuring the desired analyte. In other embodiments, the detector measures the concentration of the analyte at the sample processing cell. As illustrated in FIG. 2E, one embodiment of the instant invention utilizes a combination cell Z' as both the processing cell and measurement cell. Source L' delivers optical radiation to the combination cell Z' via an optical guide 140' and the optical detection mechanism 145' detects the output by guide 142'. In this configuration the reservoir 164 and pump 166, FIG. 2A, are in line with the combination cell Z', FIG. 2E, by valve 112, FIG. 2A, but may be in line with valve 113 or other valves. In further embodiments valves 112, 113 and 162 may be combined all or in part.

In yet another embodiment, the device measures at one or more spots along the sample processing cell. As illustrated in FIG. 2F, measurement takes place at sites Za, Zb and Zc, each sites connected to a guides from a source and measurement device. Measurement may be taken with a single source and single device with the guides being split and delivered to sites Za, Zb and Zc in turn and as known in the art. Or measurement may be performed with one or more sources and one or more devices, each with guides to and from the measurement sites (neither illustrated for simplicity). In such a construction, each measurement site has a homogenous equilibrium state between sample and processing liquid. For example, the second conduit has at least a single analyte-permeable wall on one plane (e.g. horizontal) and two measurement windows across from each other in two walls in another plane (e.g. vertical walls), perpendicular to the flow, allowing for measurement at a discrete, equilibrium homogenous sample site.

Pump Mechanism

The instant invention includes at least one pumping mechanism. The pumping mechanism may comprise any displacement means capable of moving a fluid from one tube or space to another, including but not limited to, a pump, a peristaltic pump, a displacing mechanism driven by gravity, pressure, vacuum, or physical displacement. In one construction, the continuous DIC measuring system 100, FIG. 2A, includes four pumping mechanism, referred simply as pumps. In the currently high-precision digital peristaltic pumps (Ismatec® SA, Switzerland) for pumps 109, 116, 138 and 166, a micro-volume, 10 mm optical 'Z' cell (SMA-Z-10-uvol; FIAlab Instruments Inc.) for measurement cell Z, an Ocean Optics USB4000 spectrometer for spectrophotometer 145, and a white LED light source (LE-1W-CE; WT&T Inc., Canada) for source L. Other metering pumps or pump models tested for volumetric precision are also suitable. In the currently preferred embodiment, the sample processing cell 60' was assembled with a 120 cm piece of Teflon AF 2400 capillary tubing (0.5 mm O.D. by 0.4 mm I.D.) and various commercial PEEK fittings and tubing (1.6 mm O.D. and 0.5-1.0 mm I.D.; Upchurch Scientific). In some embodiments, the capillary tubing is less than 120 cm in length, in one embodiment less than 100 cm and, in another embodiment, less than 50 cm in length. In other cases, a capillary tube greater than 120 cm is desired. Additionally, the capillary tubing may be decreased in diameter to less than 0.4 mm internal diameter, or in some cases increased to an internal diameter greater than 0.4 mm up to 1 mm or more. In further embodiments, the sample processing cell is a membrane chosen for its permeability selective for specific substances. For example, chitosan membranes with pretreated (e.g. alkalified) sample liquids as described in Barakat 2018.

For the results depicted in FIGS. 3-8B, the optical signals were monitored and recorded using a laptop PC and the Ocean Optics SpectraSuite software. In other embodiments, the signals produced by the system are recorded in an incorporated microprocessor (e.g. a controller). The system 100, with all of its reagents and fluid (e.g., seawater) samples or standards, was thermostated at 25.0±0.1° C. with a water bath and a custom-made, air-circulated Peltier device. Flow-through seawater was pumped through a coiled sample processing cell to facilitate temperature equilibration. In some constructions, the system 100 performs measurements at a range of temperatures including less or equal to than 0° C., less than 10° C., less than 25° C., greater than 25° C., and in some cases up to or greater than 100° C. Additionally, the system may operate in an unregulated internal temperature environment. In some constructions, system 100 or system 200, FIG. 2B, are part of a larger system 400, FIG. 2D.

In another embodiment, the system 200 further comprising one or more sensing mechanisms. The sensing mechanism may be a probe pH meter, a conductivity sensor, a selective intellical probe (commercially available from Hach Company, Loveland Colo.), and the like, all well known in the art The CHANOS pH channel 300, FIG. 2C, uses a flow-through design in which seawater or other sample liquid directly and continuously mixes with an processing solution. It is based on the well-established spectrophotometric pH method, where dissociation of the added sulfonephthalein indicator (H2I) in seawater is dominated by $$HI^- \xrightleftharpoons{K_I} H^+ + I^{2-};$$

$K_I$ is the dissociation constant of the indicator acid species $HI^-$. Combining Beer's Law, seawater pH can then be expressed as:

$$pH = pK_I + \log \frac{R - e_1}{e_2 - Re_3}, \tag{6}$$

where 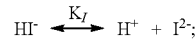, and $\lambda_1$ and $\lambda_2$ are the wavelengths for the absorbance maxima of $HI^-$ and $I^{2-}$; $e_1$, $e_2$, and $e_3$ are indicator molar absorbance ratios at wavelengths $\lambda_1$ and $\lambda_2$:

$$e_1 = \frac{\lambda_2 \epsilon_{HI}}{\lambda_1 \epsilon_{HI}}, e_2 = \frac{\lambda_2 \epsilon_I}{\lambda_1 \epsilon_{HI}}, e_3 = \frac{\lambda_1 \epsilon_I}{\lambda_1 \epsilon_{HI}}, \tag{7}$$

where $_{\lambda_1}\epsilon_I$ and $_{\lambda_2}\epsilon_I$ are the molar absorbances of $I^{2-}$ at wavelengths $\lambda_1$ and $\lambda_2$, and $_{\lambda_1}\epsilon_{HI}$ and $_{\lambda_2}\epsilon_{HI}$ refer to the molar absorbances of $HI^-$ at wavelengths $\lambda_1$ and $\lambda_2$. The indicators used in this the processing solution included thymol blue sodium salt ($\lambda_1$=435 nm and $\lambda_2$=596 nm) and m-cresol purple sodium salt ($\lambda_1$=434 nm and $\lambda_2$=578 nm), but may be any suitable pH indicator or colorimetric reagent. A non-absorbing wavelength (700 nm) was used to correct baseline changes. Calibrations of $pK_I$, $e_1$, $e_2$, and $e_3$ of the two indicators for typical seawater temperature and salinity have been established in laboratory experiments. It has been demonstrated that in situ spectrophotometric pH measurements require infrequent or no calibration.

Figure 2D:
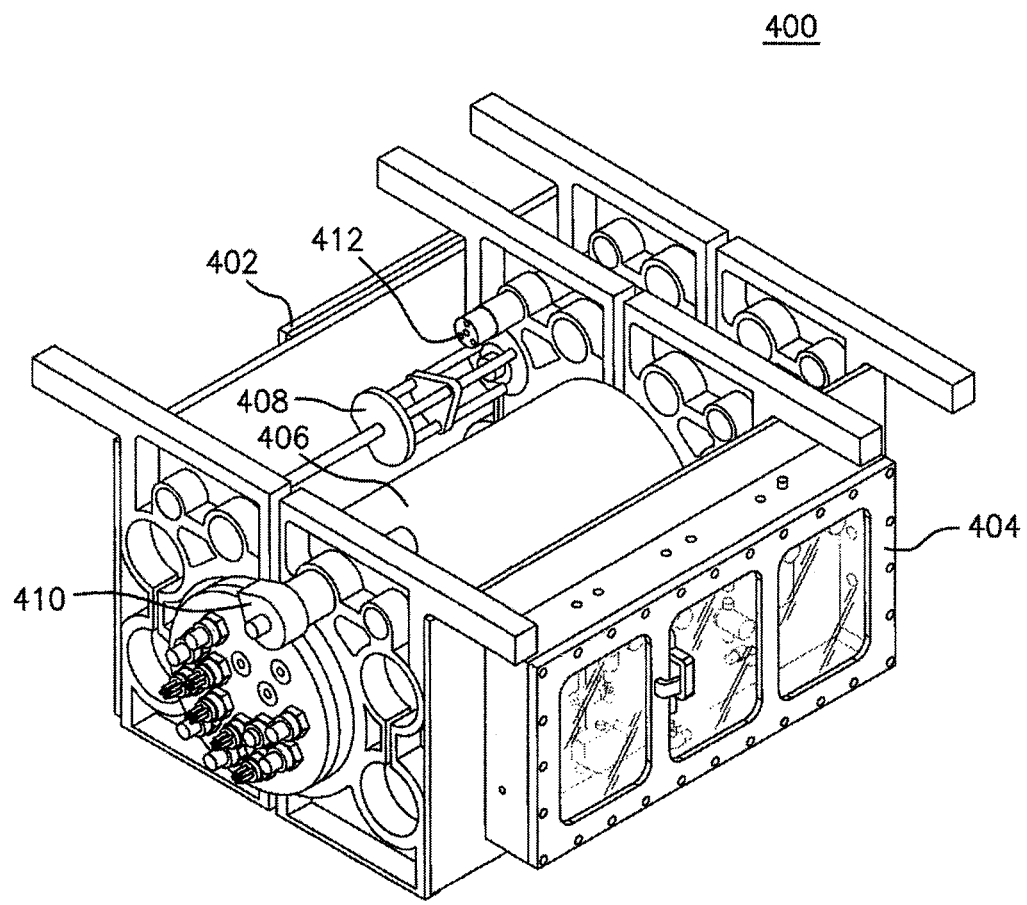
FIG. 2D is a schematic perspective illustration of the CHANOS which includes the channels depicted in FIGS. 2B and 2C.
Figure 2E:
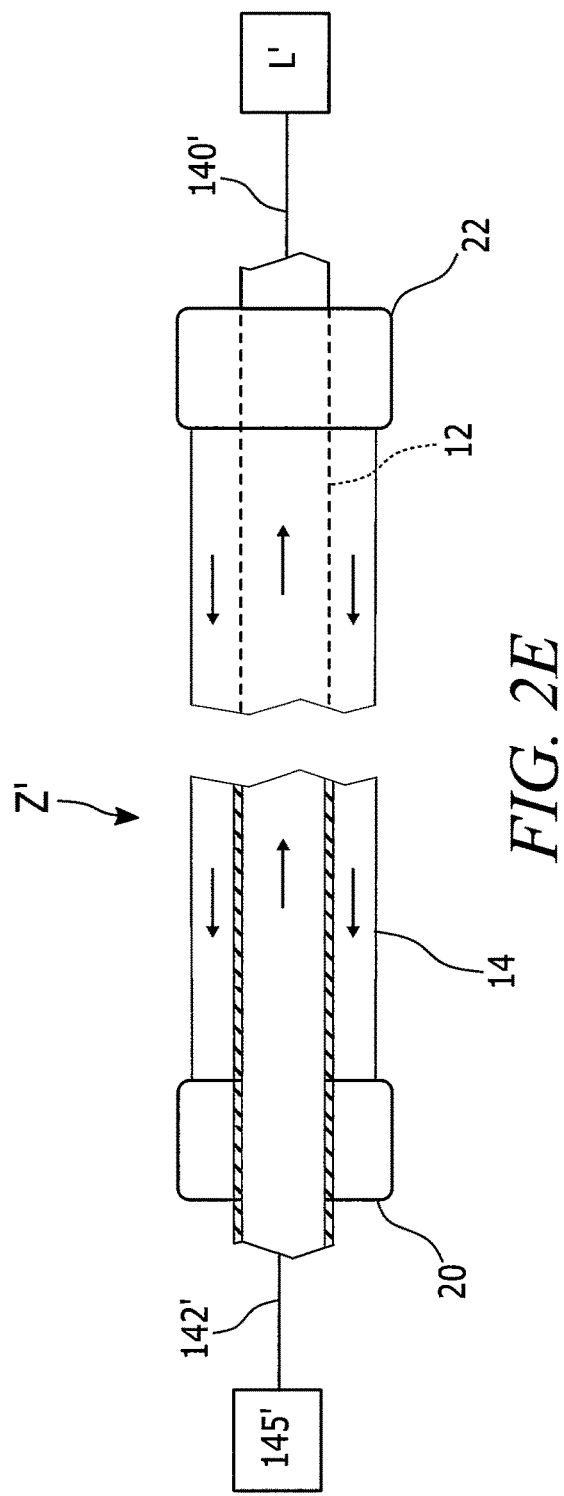
FIG. 2E is a schematic block diagram of a system according to the present invention utilizing one of a concurrent or countercurrent flow.
Figure 2F:
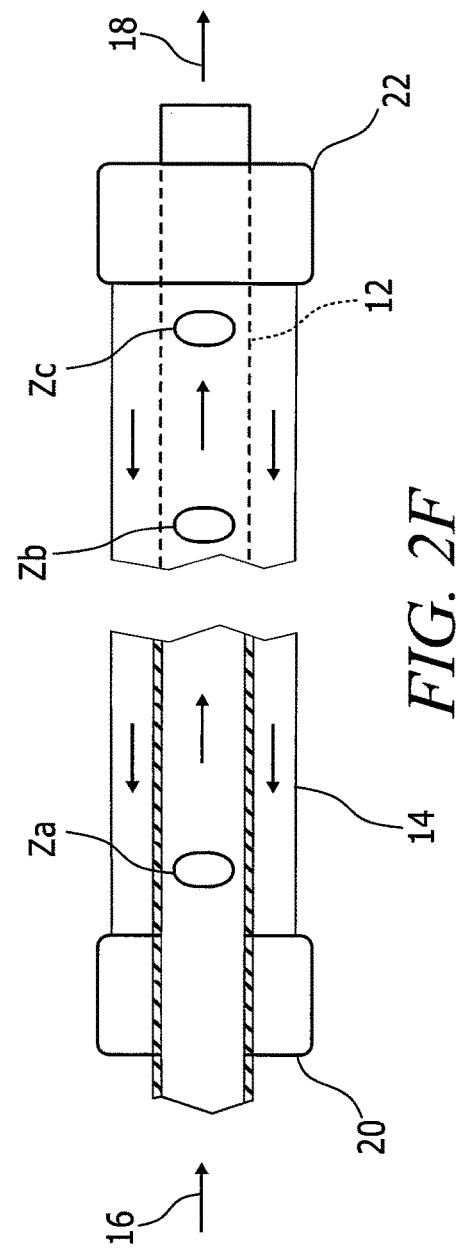
FIG. 2F is a schematic, partial cross-sectional view of a sample processing cell utilized according to the present invention for measurement of discrete, homogenous equilibrium states of sample and processing fluid.

In one construction, CHANOS 400, FIG. 2D, consists of four major components: two junction boxes (J-boxes) 402 and 404, each configured to perform at least one measurement. In the currently preferred embodiment, one J-box measures pH and one measures DIC, respectively, a pressure housing 406, four custom-made stepper-motor syringe pumps 408, and a pump 410 such as a Seabird Model 5P. Each J-box 402, 404 contains one 2-port and one 3-port solenoid valve (161K011, T161PK031, NResearch Inc.), a sample diaphragm pump (NF5, KNF Group International), thermistors, and optical and fluid handling components (FIGS. 2B and 2C). J-box components and pH Measurement Cell 412 are described in more detail below. Infusion pumps, metering pumps, peristaltic pumps, syringe pumps or other pump models tested for pressure resistance and volumetric precision are also suitable.

The pressure housing 406 contains all of the controlling electronics, light sources, and the primary optical detection system. The controlling software runs on a controller (e.g. a TERN microprocessor) as described in more detail below.

Four custom-made syringe pumps 408 were made using high precision stepper motors (Phytron, Model ZSS 25-GPL26). In one construction, a Seabird pump 410 is used to pump sample water through a coarse copper mesh filter (preferably mesh size 100 μm but may be less than 100 μm or in some cases greater or equal to 200 μm), and each channel then subsamples water through an additional copper mesh filter (preferably mesh size 40 μm but may be less than 40 μm, less than 80 μm, or less than 100 μm) to reduce fouling within the system. Although other filters may be used, the copper filter is particularly adapted for the marine environment, resisting fouling on the filter itself. In some embodiments, the filter is coated with an anti-fouling coating. Discrete bottle measurements confirmed that there was no detectable difference between mesh-filtered and non-filtered samples for local coastal waters (mean difference 1.6±3.5 μmol kg$^{-1}$, n=9).

Figure 14A:
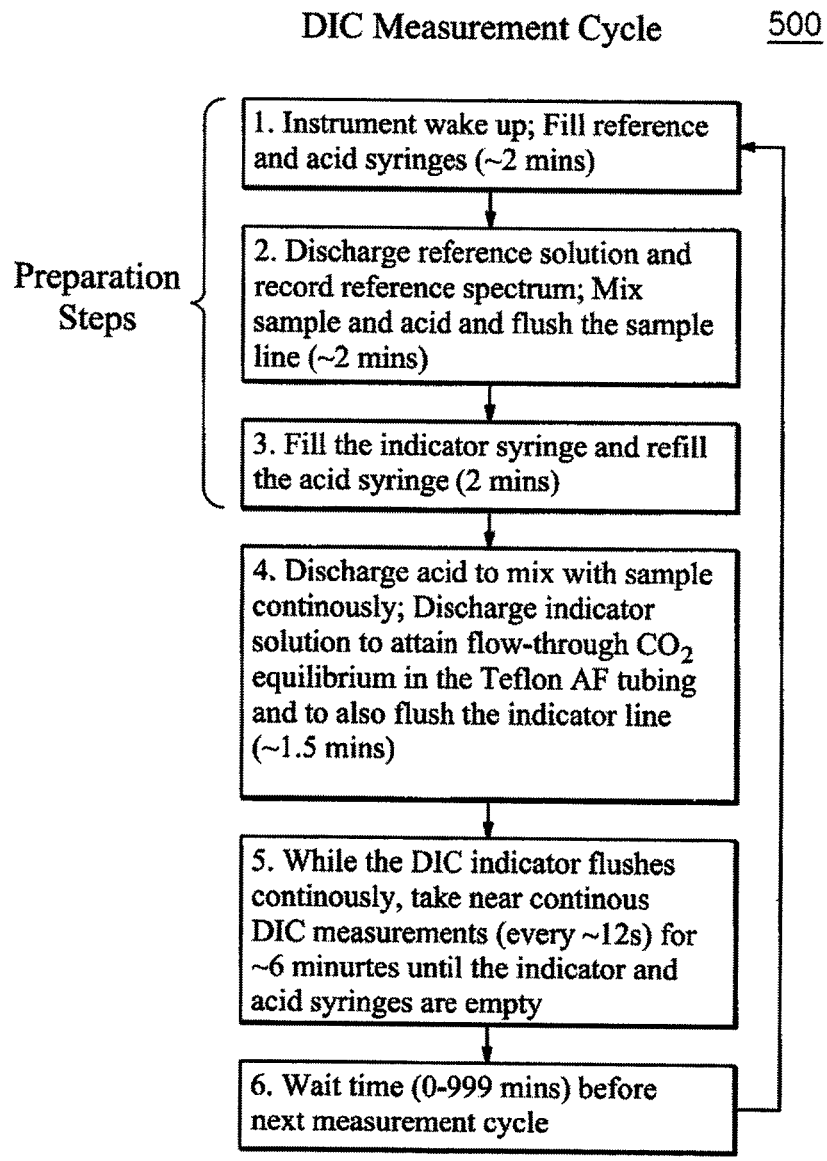
FIGS. 14A and 14B are flow charts of customizable DIC and pH running cycles for CHANOS.
Figure 14B:
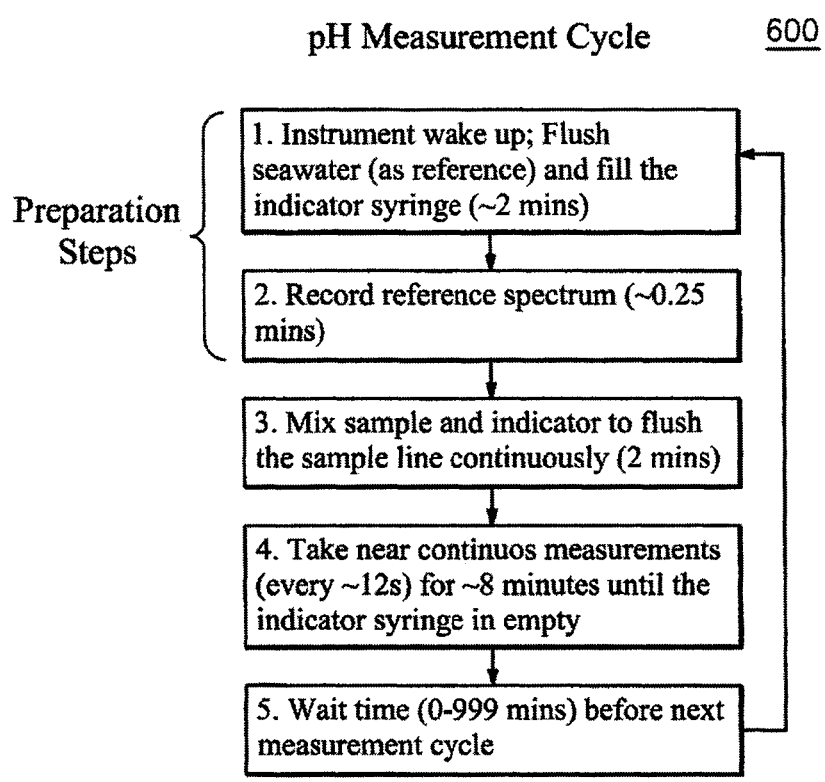

CHANOS runs on repeatable cycles, which include a series of mission steps for both channels as discussed in more detail below regarding FIGS. 14A and 14B. For the DIC measurement cycle, measurement preparation steps include filling the pretreatment, reference, and processing solution syringes, flushing the pretreated sample and reference, and recording a reference spectrum (FIGS. 14A and 14B). Thereafter, processing solution flows continuously through the Z-cell while pretreatment solution (e.g. acid) continuously mixes with sample water and flows through the sample line until the processing solution and pretreatment syringes are emptied. Stable readings are achieved after the processing solution has flowed for approximately 90 seconds. Thereafter, the system records approximately 6 minutes of spectra with near continuous measurements (less or equal to about 12 s per measurement). Changes in the measurement cycle and size of the syringes can allow for higher resolution measurements as discussed in more detail below. The cycle is similar for in situ calibration, except that CRM is used in place of an external sample (FIG. 2B). For the pH channel, similar preparation steps take place before near continuous measurements (less or equal to about every 12 s for about 8 minutes) commence (FIGS. 14A and 14B). At a selected or pre-determined interval (e.g., once per day, or every few days), the pH channel is flushed with a Triton 100 detergent solution for cleaning purposes and reduce fouling within the system. For all channels, all steps are customizable depending on deployment purposes.

For DIC reagents, bromocresol purple ("BCP") sodium salt (Sigma-Aldrich) was used to make 4 mM indicator stock solutions that were stored in opaque glass bottles at 4° C. Working processing solutions were prepared from the indicator stock solutions with a final concentration of 20-30 μM. This concentration, about 10 times that of the previous work (2-3 μM), was required to produce optimal absorbances with the short pathlength 'Z' cell. The alkalinity of the processing solutions was established by adding extra-pure $Na_2CO_3$ (Acros Organics). Final TA concentrations of ~700-800 μmol kg$^{-1}$ were chosen so that the final processing solution pH for measurements of typical seawater DIC concentrations fell within the range of ~5.6-6.4, where the indicator absorbance change is sensitive. This is similar to what has been achieved in the intermittent method. For each liter of processing solution, 0.5 ml of 10% lauryl sulfate sodium salt solution was added to serve as a surfactant for cleaning purposes. Reference solutions were prepared using an identical procedure to the processing solutions but without added indicator. The working processing solution and reference solutions were enclosed in 2 liter analyte-impermeable laminated bags (Calibrated Instruments, Inc.). Bagged solutions can last several months without any appreciable changes in composition. In one embodiment samples were acidified during pretreatment with hydrochloric acid (HCl, 2.5 M).

Sodium carbonate solutions and Certified Reference Materials (CRMs) were used as DIC standards. The former were made with ultra-purified sodium carbonate (Sigma-Aldrich) in appropriate ionic strength sodium chloride solutions corresponding to various seawater salinities. They were stored in 1 L borosilicate glass bottles and poisoned with saturated mercuric chloride ($HgCl_2$). The DIC values of these standards were ascertained to within ±2.0 μmol kg$^{-1}$ using a NDIR-based DIC auto-analyzer (AS-C3, Apollo SciTech) that was calibrated with CRMs. The DIC concentrations were corrected for the dilution effect of $HgCl_2$ and density. CRMs were also stored in 2 liter analyte-impermeable laminated bags (Calibrated Instruments, Inc.) used for in situ calibrations.

The NDIR-based DIC analyzer (AS-C3, Apollo SciTech) uses an inert gas (nitrogen) to purge $CO_2$ gas from a known amount of pretreated seawater sample; the $CO_2$ in the resulting gas stream is quantified by a NDIR $CO_2$ analyzer (LI-7000, LI-COR). The calibration of the analyzer was conducted using CRMs on a twelve-hour interval. This instrument has a precision and accuracy of better than ±2.0 μmol kg$^{-1}$.

For the pH channel, thymol blue (TB) sodium salt (Sigma-Aldrich, ACS Certified) was used to make working processing solutions with concentrations between 1.5-2.0 mM. TB is well suited for pH≥7.9 which is often observed in the local waters where the deployment occurred. The R ratio of the processing solution was adjusted (R~0.77) to minimize indicator-induced pH perturbations. The pH indicator solution was also stored in a laminated bag. The sample-to-processing solution mixing ratio was maintained at ~700:1, so that the final processing solution concentration was approximately 2-3 μM. The indicator perturbation was generally smaller than ±0.002, and was corrected based on the standard procedure. The pH measurements were also corrected for the impurity of the indicators based on the recommended method through comparison with purified m-cresol purple (mCP) sodium salt.

The DIC measurement procedure is summarized as follows: (1) Seawater samples or DIC standards were acidified with HCl at a water-to-acid mixing ratio of ~700:1, and then directed to flow through the countercurrent flow cell outside of the Teflon AF tubing at a flow rate of ~4.0 mL min$^{-1}$ (FIG. 2A); (2) The measurement cell was flushed with reference solution and a reference spectrum was taken; (3) processing solution was pumped at a selected flow rate, as described in more detail below, through the countercurrent flow cell (inside the Teflon AF tubing) in the opposite direction as the seawater, and the processing solution exited the countercurrent cell after $CO_2$ exchange and flowed through the measurement cell for absorbance detection at a frequency of ~1 Hz; and (4) Reference was retaken regularly to correct any potential absorbance baseline drift.

Calibration of the DIC system was necessary to establish a quantitative relationship between $$\frac{[DIC]}{(K_0)_a}$$

and $(fCO_2)_i$ under the selected running conditions. The CHANOS can make DIC measurements using either partial or full $CO_2$ equilibrium. If partial equilibrium is used for measurements, the calibration involved two steps for each batch of bromocresol purple processing working solution. First, the system was calibrated with CRMs to obtain the B(t) constant in Eq. 5 by running the processing solution at a slow speed (<0.03 mL min$^{-1}$), which allowed the processing enough time (>5 minutes) inside the Teflon AF tubing to achieve 100% $fCO_2$ equilibration (p=1 in Eq. 3). B(t) was later used to calculate $(fCO_2)_i$ (the right side of Eq. 5) for standard runs at the higher selected indicator flow rate. Note that B(t) reflects chemical and optical properties of the processing solution (Eq. 4), and does not change with processing solution flow rate. Secondly, more than 5 DIC standards were measured at the same faster processing solution flow rate to obtain the absorbance ratios in Eq. 5 corresponding to partial $fCO_2$ equilibration of each standard. $(fCO_2)_i$ was then calculated from Eq. 5 to establish a $(fCO_2)_i$ vs.

$$\frac{[DIC]}{(K_0)_a}$$

curve. Sample water was run at the same conditions as the DIC standards to obtain R. The sample DIC concentrations were calculated using B(t), R, and the calibration curve. In this procedure, the variable p is built into the calibration curve as described in more detail below. If full equilibration is used for measurements, only the first calibration step is conducted to obtain B(t). Laboratory testing was conducted to establish calibration and measurement characteristics of the new method as well as to try to optimize running conditions. Thereafter, the continuous DIC system, FIG. 2A, was tested at the Environmental Systems Laboratory at Woods Hole Oceanographic Institution (WHOI), Woods Hole, Mass., USA for measurements of flow-through seawater that was pumped from a mile offshore. This test was conducted in June 2012 over three days. To groundtruth the new DIC method, traditional discrete DIC bottle samples were collected simultaneously with continuous DIC measurements. The samples were poisoned and measured using a NDIR-based DIC auto-analyzer. The new DIC system was further tested using discrete bottle samples that were collected from three hydrographic stations up to 3000 m in depth using a Conductivity-Temperature-Depth (CTD) Rosette Niskin Bottle package in August-September 2012 during a cruise in the North Pacific. The samples were collected in 1 L borosilicate glass bottles and poisoned with saturated mercuric chloride. Each sample was pumped through the DIC system for continuous measurements over a period of 15-20 minutes. Duplicate bottle samples were also collected into 250-ml borosilicate glass bottles following the same sampling procedure for the NDIR-based DIC measurements to gauge the new system's performance. All bottle samples were analyzed within two weeks.

A multi-channel system 400 according to another embodiment of the present invention, FIG. 2D, is an in situ DIC-pH sensor Channelized Optical System (CHANOS), capable of simultaneous spectrophotometric measurements of seawater DIC, FIG. 2B, and another parameter such as pH via a conventional pH sensor in system 300, FIG. 2C. The CHANOS is among the first sensor system that is able to fully resolve carbonate chemistry with a single system and a desirable pair of $CO_2$ system parameters measured to achieve small calculation errors. The CHANOS preferably has a build-in mechanism for in situ calibration, which ensures high measurement quality throughout a deployment and reduces the need for laboratory calibration. Preferably, the system is able to make high-resolution, climatology-quality measurements to resolve seawater-$CO_2$ system dynamics.

In one construction, the DIC channel portion of system 200, FIG. 2B, includes three custom-made high-precision stepper motor syringe pumps for the pretreatment pump, the processing solution pump and the reference fluid pump, a diaphragm pump for delivering the sample liquid to the equilibration cell, a micro-volume, 10 mm optical 'Z' cell (SMA-Z-10-uvol; FIAlab Instruments Inc.) for optical Z-cell, an Ocean Optics USB4000 spectrometer for spectrophotometer 145, and a custom-made white LED light source for source L. In one construction, the countercurrent flow cell is assembled with a 120 cm piece of Teflon AF 2400 capillary tubing (0.5 mm O.D. by 0.4 mm I.D.) and various commercial PEEK fittings and tubing (1.6 mm O.D. and 0.5-1.0 mm I.D.; Upchurch Scientific). The optical signals were monitored and/or recorded internally on a storage medium such as a flash drive using custom-made software.

The DIC Junction Box (black line box) with all its items are filled with a suitable conventional oil and sealed from the outside environment to provide protection and pressure compensation in water. The LED light, spectrophotometer, and all electronic components are placed in a water-tight pressure housing, such as housing 406, FIG. 2D. All custom-made syringe pumps are water-proof.

Figure 3:
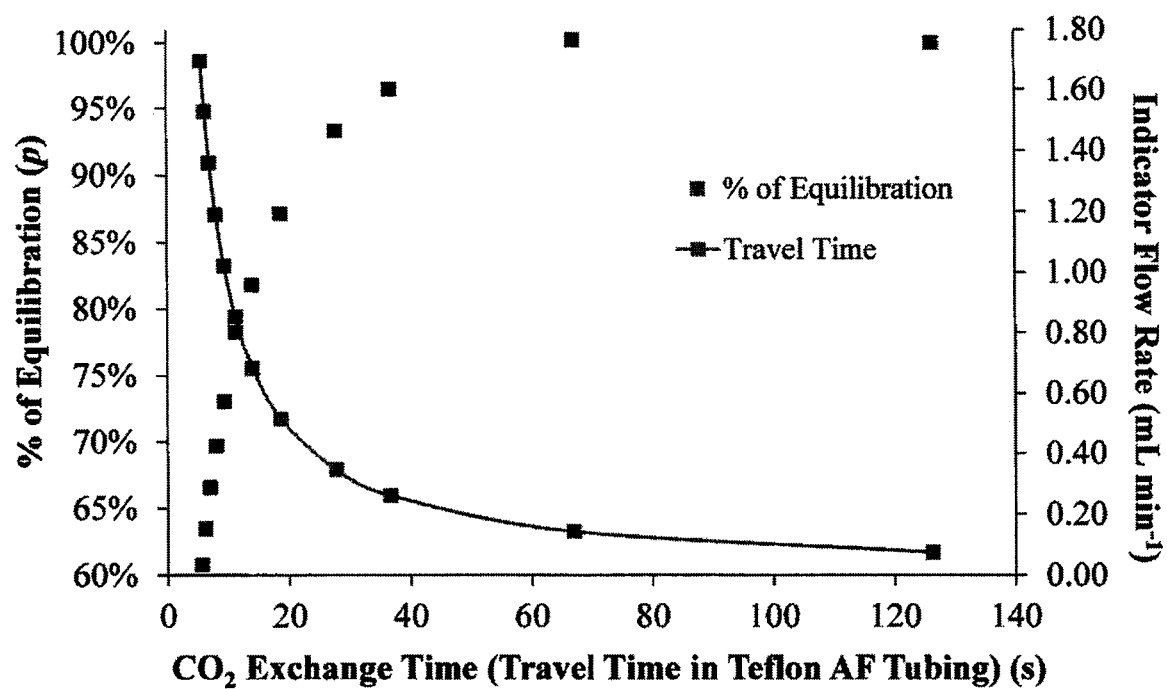
FIG. 3 is a graph showing the percentage of equilibration and processing solution flow rate as a function of $CO_2$ exchange time.

Regarding measurement characteristics, FIG. 3, the percentage of $CO_2$ equilibration (p) is a function of processing solution flow rate or travel time through the 120 cm long Teflon AF tubing for the systems of FIGS. 1B and 2A. Travel time is the amount of time that it takes for the processing solution to travel the length of the Teflon AF tubing. This is also equivalent to $CO_2$ exchange time, the amount of time that the processing solution exchanges $CO_2$ with the pretreated sample. The variable p increases non-linearly with an increase in $CO_2$ exchange time. A higher processing solution flow rate would allow for less travel time in the Teflon tubing for $CO_2$ exchange, resulting in lower $CO_2$ equilibration, faster response time, and greater processing solution consumption. At very high flow rates, the optical detection becomes noisy probably due to increased pulsing from the peristaltic pump, causing unsteady flow in the measurement cell. Travel time or $CO_2$ exchange time inside the Teflon AF tubing with a fixed internal volume is proportional to the reciprocal of processing solution flow rate (FIG. 3). Benchtop testing utilized an processing solution flow rate of ~1 mL min$^{-1}$, equivalent to a 9 s $CO_2$ exchange time, which is an effective balance between processing solution consumption, response time, and detection stability. A further increase in processing solution flow rate would not significantly decrease $CO_2$ exchange time. The system can reach 100% equilibration for a travel time of ~70 s, which is more than 4 time faster than the intermittent method.

Figure 4A:
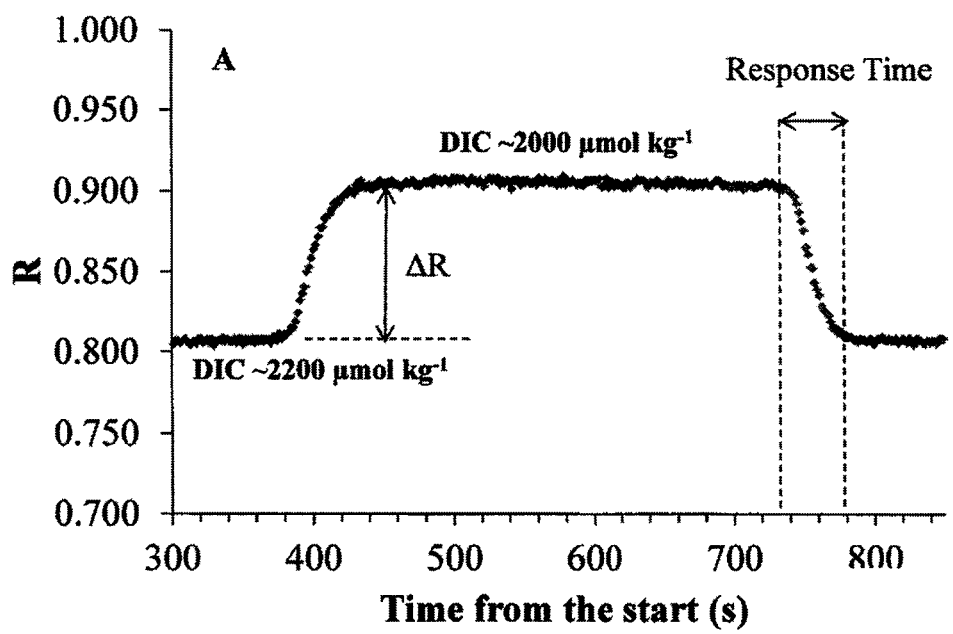
FIG. 4A is a graph of processing solution response to absorbance ratio as a function of time, at the same running conditions as for FIGS. 4B-8B.
Figure 4B:
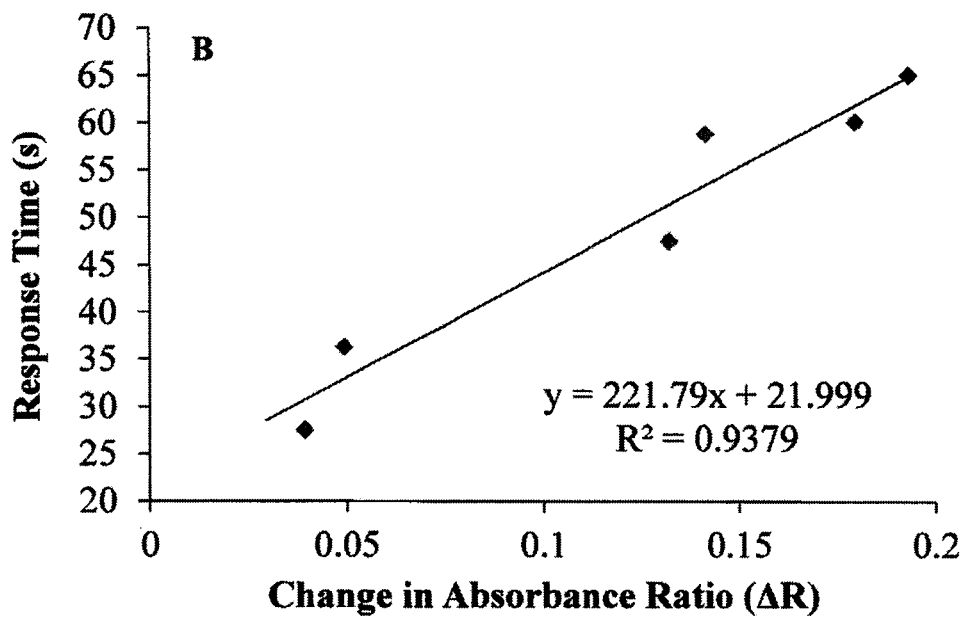
FIG. 4B is a graph of response time as a function of change in absorbance ratio.
Figure 5:
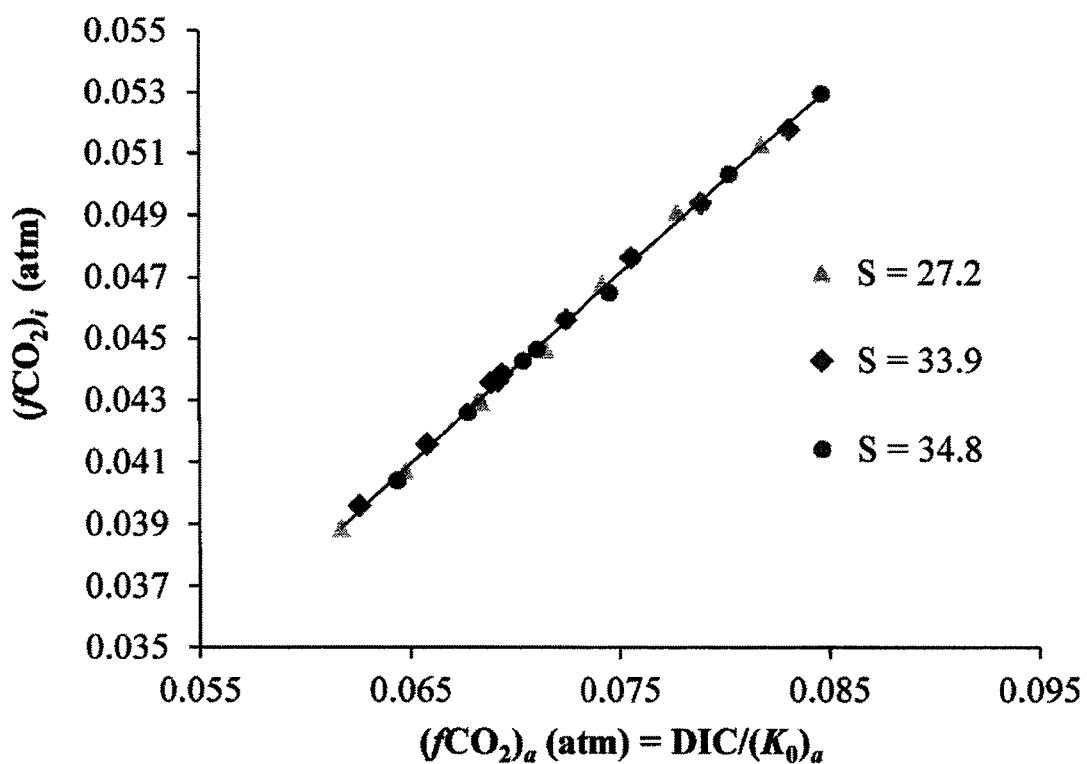
FIG. 5 is a graph of calibration data for DIC (Dissolved Inorganic Carbon) using standards with three different salinities.
Figure 6:
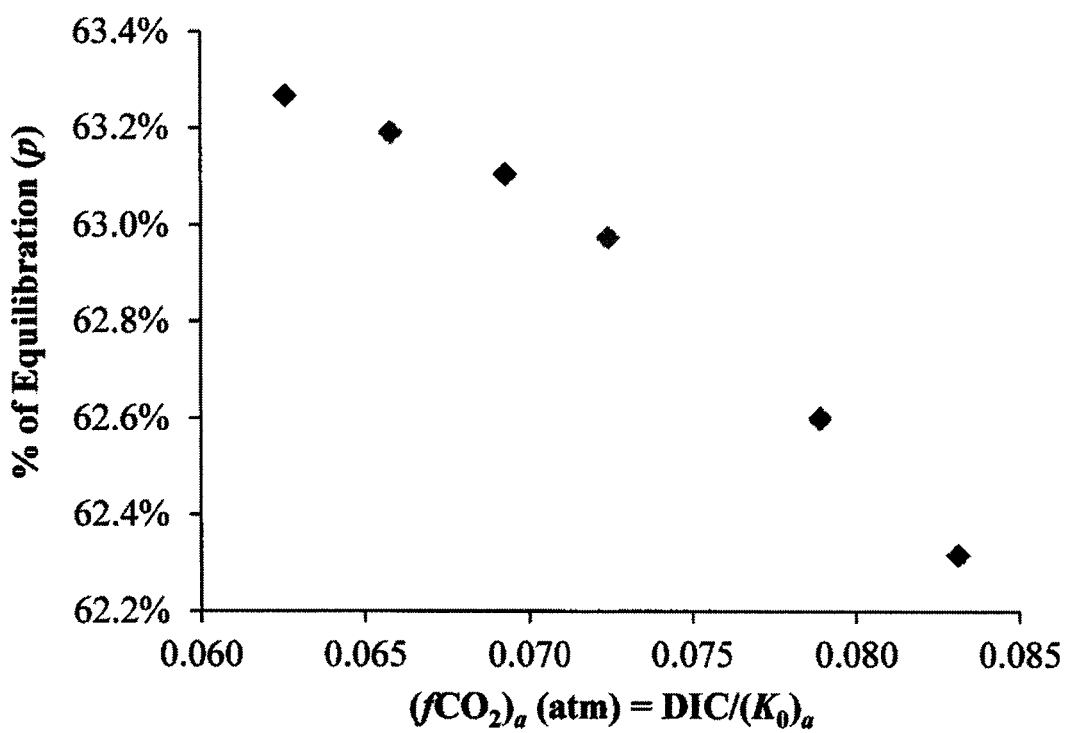
FIG. 6 is the percentage of equilibration across Teflon AF tubing as a function of $fCO_2$ in the pretreated sample.

At the current settings with partial equilibrium, it takes approximately 35-60 seconds to achieve a steady response at 25.0° C. while varying between two samples with DIC concentrations in the range of approximately 1800-2400 µmol kg$^{-1}$ (e.g. FIG. 4A). The response time only varies by a few seconds for a given change in absorbance ratio under the same running condition. There is a significant linear relationship between response time and changes in absorbance ratios when switching between two DIC samples (FIG. 4B). The response time is much longer than the $CO_2$ exchange time of ~9 s under the current settings. The discrepancy between the two is likely due to the time that is required to flush the Teflon tubing and the measurement cell with new processing solution. Because of laminar flow throughout the flow path, the volume needs to be replaced several times before it is completely flushed. This explanation is consistent with the fact that the response time becomes shorter when ΔR, or the concentration difference between the two samples, decreases (FIG. 4B). The intercept in FIG. 4B thus approximately represents an actual response time of ~22 s during flow-through measurements, when sample concentration change is incremental as opposed to large changes as shown in FIG. 4A. The response time can be further improved by reducing the internal volume in the processing solution flow path to reduce the effect of laminar flow.

The current response time (~22 s) is more than one order of magnitude faster than that in the intermittent method (~5 mins) with static, full equilibration. The data does not show that there is an apparent difference in response time between the countercurrent and concurrent flow under the current partial equilibrium settings. This may be because a large portion of the response time results from the time that it takes to flush the system. However, the countercurrent flow can achieve a slightly higher $CO_2$ diffusion efficiency by a few percentages for a 9 s $CO_2$ exchange time.

In the present method, the signal change for a 9 s $CO_2$ exchange time is ~92% of the total signal change if the processing solution reached full equilibrium. However, the same exchange time using static equilibration in the intermittent method only allows for ~65% of the total signal change. As such, the dynamic equilibration can achieve a 40% increase in equilibration efficiency as compared to static equilibration. It would take about 60 s with static equilibration to reach the same total signal change of 92%. Therefore, $CO_2$ equilibration in the continuous method is 6 times faster than that in the intermittent method. It is impractical to use partial equilibration in the intermittent method since the signal associated with a short exchange time (e.g. 9 s) would fall on a sharp changing slope, resulting in an unstable and inconsistent recording, and would have large measurement errors. For dynamic partial equilibration in the continuous method, a stable and consistent signal is reached before recording (FIG. 4A). Under the current settings, the variability in absorbance ratio (R) when measuring a stream of water with a constant DIC is only ~±0.0017 (1 σ), which translates to a DIC analytical uncertainty (short-term precision) of ±2.0 µmol kg$^{-1}$.

Calibration curves for the continuous DIC method (FIG. 5) were derived over the DIC range encountered in samples with an processing solution flow rate of 1.0 mL min$^{-1}$ and a sample flow rate of 4.0 mL min$^{-1}$ at a temperature of 25° C. The data in FIG. 5 were obtained from three series of calibrations at three different salinities using the same processing solution and running conditions. Each series of calibration generates a polynomial equation, with a standard error of ±1.0-3.0 µmol kg$^{-1}$, comparable to the measurement precision (±2.0 µmol kg $^{-1}$). The effect of varying the salinity of the DIC standards has no measurable effect on the calibration curves in FIG. 5. This is because the salinity effect on $(fCO_2)_a$ has been accounted for since $(fCO_2)_a$ was calculated from DIC values and $(K_0)_a$ (Eq. 1), and the latter is a known function of salinity. Internally, salinity for a given processing solution is low (S~0.05) and constant. Beyond the effect on $(K_0)_a$, salinity did not have a measurable effect on the calibration curves in the salinity range encountered. Three individual calibration curves and the calibration curve containing all of the data in FIG. 5 had a pooled mean difference of 0.5±3.4 µmol kg $^{-1}$. This is within the 95% confidence interval of measurement uncertainties.

Under fixed running conditions with a particular processing solution, the variable p is a function of the $fCO_2$ gradient between the pretreated sample and the processing solution. The slight convex of the calibration curve in FIG. 5, demonstrates that p varied over the $(fCO_2)_a$, or DIC, range (p represents the slope of the curve as defined in Eq 5). As $(fCO_2)_a$ in samples increases, p decreases under the same running conditions for the results shown in FIG. 6. This can be explained conceptually as follows: the $fCO_2$ gradient across the Teflon AF tubing increases as $(fCO_2)_a$ increases; for a given processing solution flow rate (thus a fixed time for $CO_2$ exchange inside the Teflon AF tubing), p decreases with an increase in the sample-processing solution $fCO_2$ gradient. However, this effect is relatively small at the selected running conditions (FIG. 6): p only changes by ~1.0% in the $(fCO_2)_a$ range corresponding to a DIC range of 1780-2370 µmol kg$^{-1}$. This effect can be fully accounted for in the system calibration using the curve of FIG. 5.

Figure 7A:
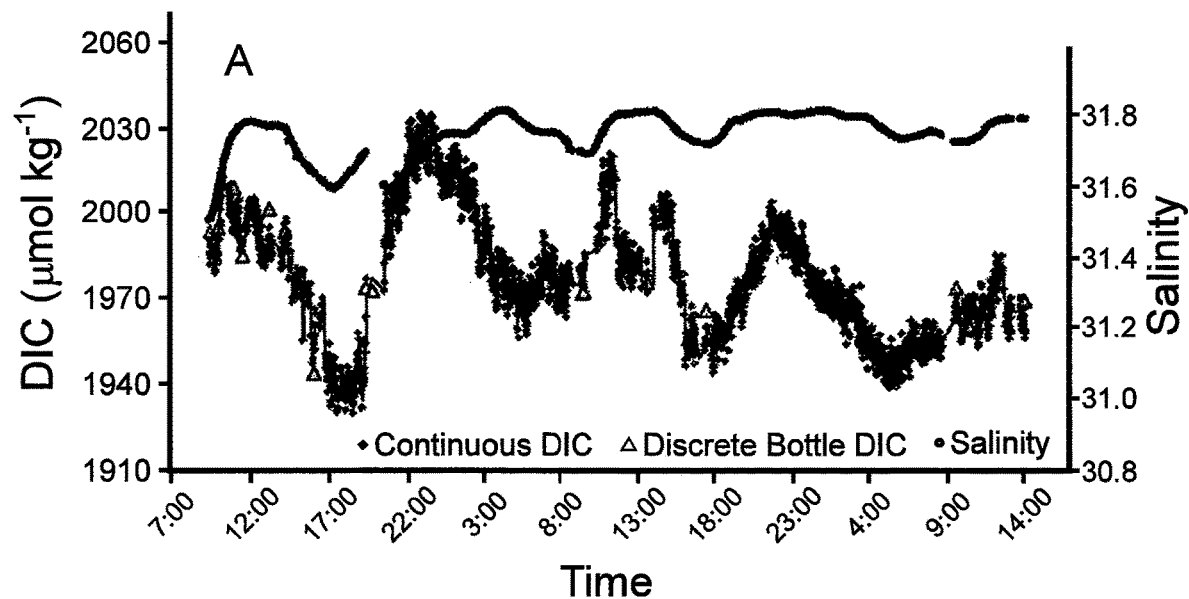
FIG. 7A is a graph of continuous seawater DIC measurements according to the present invention along with flow-through salinity and discrete DIC bottle measurements at different time periods.

Field testing conducted at WHOI Environmental Systems Laboratory was designed to demonstrate high-frequency, high-quality measurements using the new DIC method (FIG. 7A). During the 3-day period, which spanned multiple tidal cycles, salinity of the flow-through water varied slightly (31.5-31.8), while temperature showed ~4° C. variation (16.5-20.5). DIC concentration varied moderately (1929-2035 µmol kg$^{-1}$). Salinity and DIC sometimes showed a strong correlation, while at other times no correlation was observed, which suggests complicated tidal mixing. Each DIC data point in FIG. 7A represents a mean of 1-Hz measurements over one minute intervals. The measurements captured substantial variability on both short (minutes to a few hours) and longer (hours to days) time frames.

To evaluate the precision of the continuous DIC measurements during the testing, the data in FIG. 7A were smoothed by taking running averages (n=5; ~5 minute interval as indicated by the solid line within the continuous DIC measurements in FIG. 7A). The mean residual of individual observations relative to the running average was 0.1±3.6 µmol kg$^{-1}$ (N=2332). This uncertainty is likely an upper limit since the estimate includes DIC variability within a few minutes in the flow-through seawater, the variability that may occur in coastal oceans. It may explain the slightly lower precision in the field testing compared to that in the laboratory experiment. This estimated precision is comparable to that (~3.0 µmol kg$^{-1}$) of the intermittent method under field testing.

Figure 7B:
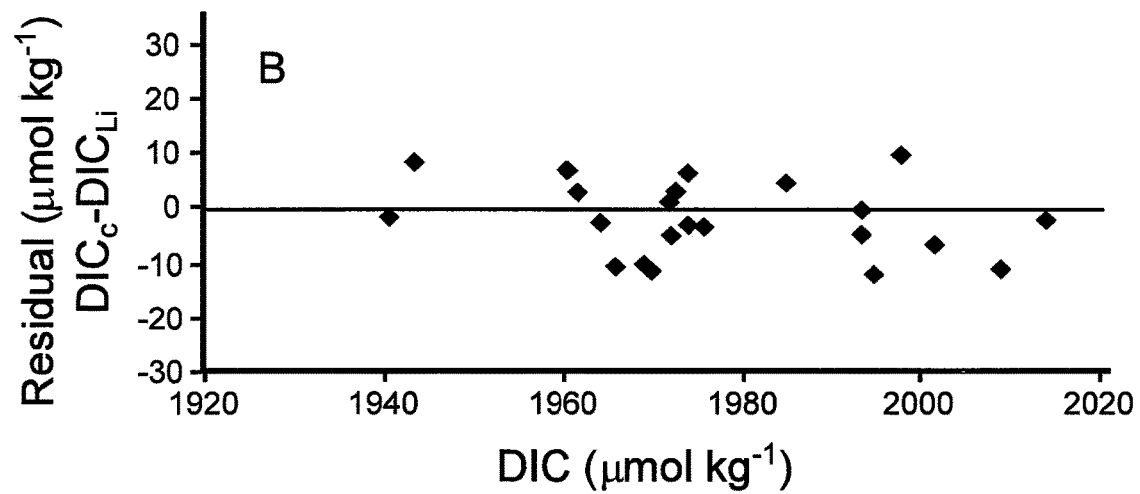
FIG. 7B is a chart of residuals between the continuous and discrete DIC measurements of FIG. 7A.

The accuracy of the continuous method was assessed by directly comparing the differences between continuous measurements and the NDIR-based bottle measurements (FIG. 7A). Both methods used standards traceable to CRMs for system calibration. Residuals between the continuous and the discrete bottle measurements did not show systematic trends (FIG. 7B). This suggests that any systematic errors in our measurements were minor. The continuous DIC measurements differ from the bottle measurements by −1.6±6.7 µmol kg$^{-1}$ (N=23). Such accuracy is similar to that in previous development. The new method thus achieved high-frequency measurements as well as accuracy and precision comparable to the existing spectrophotometric method.

Figure 8A:
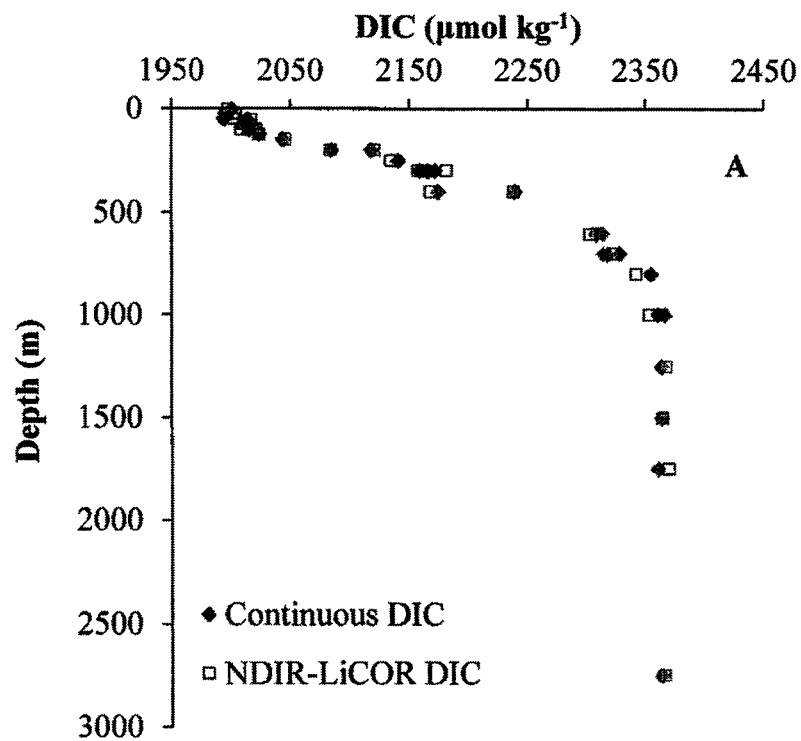
FIG. 8A is a graph of water-column DIC measurements by continuous and NDIR-based methods by depth.
Figure 8B:
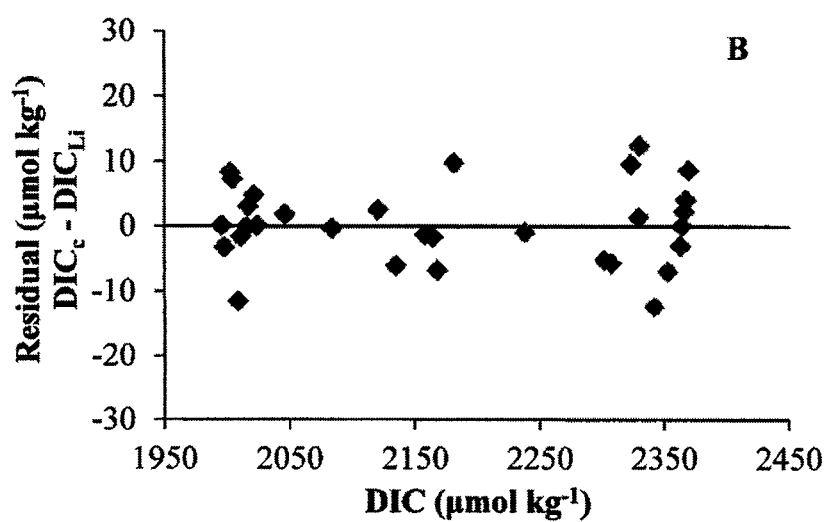
FIG. 8B is a chart of residuals between the continuous and discrete DIC measurements of FIG. 8A.

The DIC system was also used to make measurements of discrete bottle samples collected from three stations in the North Pacific at depths up to 3000 m. This test effectively captured the large DIC concentration range that may be encountered in the ocean (FIGS. 8A and 8B). In this case, DIC concentration varied from ~1990 µmol kg$^{-1}$ at the surface to ~2370 µmol kg$^{-1}$ at depth, a nearly 400 µmol kg$^{-1}$ difference (FIG. 8A). The DIC measurements by the continuous method were also in good agreement with NDIR-based analyses. The mean difference between the two methods was 0.3±6.0 µmol kg$^{-1}$ (N =31). This level of accuracy is comparable to that achieved in high-frequency measurements shown in FIG. 7. No systematic errors were observed over the DIC measurement range, as evidenced by the random distribution of the residuals between the spectrophotometric and NDIR-based measurements (FIG. 8B). This test suggests that the new DIC method can attain good precision and accuracy over a wide range of seawater DIC concentrations and in submerged conditions.

The estimated field precision (±3.6 µmol kg$^{-1}$) was about 53-60% of the field agreement estimates (±6.0-6.7 µmol kg$^{-1}$; FIGS. 7A-8B). The measurement variability resulting from the inherent noise of the new DIC system therefore accounts for ~53-60% of the variability observed in FIGS. 7B and 8B. The rest of the variability may be attributed to various external sources. These may include discrete sampling and NDIR-based analytical uncertainties. It is important to note that the level of measurement uncertainty achieved with the continuous DIC method is comparable to those of replicate bottle sample measurements using conventional DIC methods during major carbon cruises (http://cdiac.ornl.gov/oceans/).

For the CHANOS, all previously calibrated constants for spectrophotometric pH measurements (Eqs. 6-7) can be used for CHANOS pH calculations. CHANOS was tested in situ for several months in Fall 2013 at the Iselin dock of the Woods Hole Oceanographic. Institution (WHOI), Woods Hole, Mass., USA. The first several weeks were used to diagnose the overall functionality of the instrument and to make necessary changes. Thereafter, in situ measurements were made for three weeks. The sensor was programmed to make measurements every 40 minutes (FIGS. 14A and 14B). Although such a long wait time between measurements is not sufficient for capturing short time scale variability, it was sufficient for field testing.

The sensor, contained in a Pelican case, was hung in a testing well at ~5 m depth. The case provided protection to the sensor and reduced system fouling. A Seabird conductivity-temperature-depth (CTD) sensor (SBE 49) was also deployed with the sensor. A piece of Tygon tubing used for discrete sampling was co-located with the sensor sample intake for direct comparison. A field peristaltic pump was used to pump water onto the dock to collect discrete DIC and pH samples in order to assess sensor accuracy. Bottle samples were collected in 250 mL borosilicate glass bottles and poisoned with mercuric chloride following the standard procedure. Their measurements are described in Supporting Information.

The CHANOS pH channel has similar measurement characteristics as previously developed spectrophotometric pH sensors. The flow-through design allows for continuous pH measurements after taking reference spectra. The syringe pumps allow for precise delivery and therefore maintain a stable sample-to-processing solution mixing ratio during long deployments. They also minimize processing solution consumption. The self-cleaning mechanism for the pH sample line using detergent (FIG. 2C) effectively reduces fouling inside the sample tubing and maintains throughput light in the pH measurement cell. During the three week in situ testing, the light level was only reduced by approximately 10%.

Figure 9:
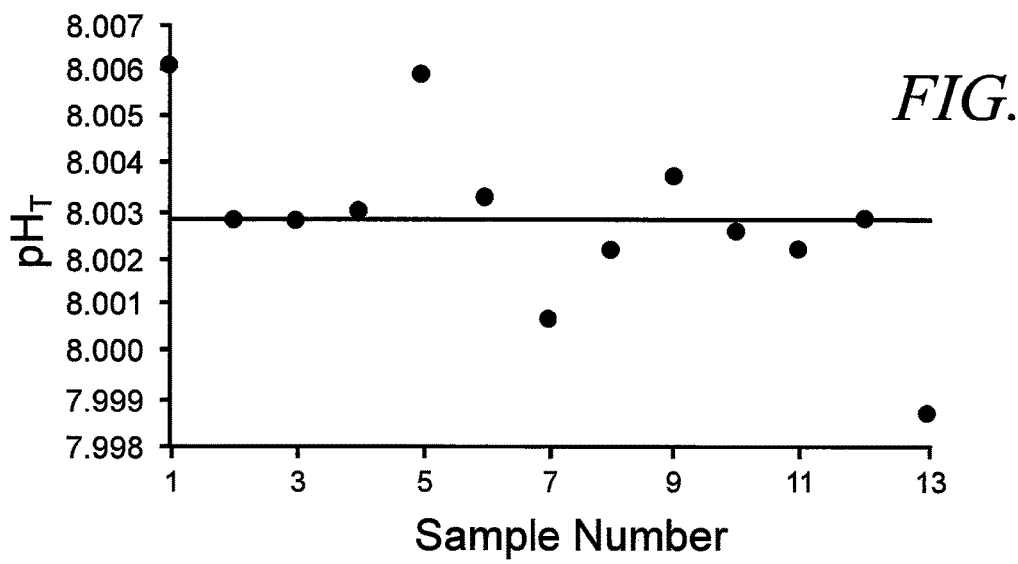
FIG. 9 is a graph of in situ repeated pH measurements of coastal waters.

Sensor performance was evaluated in the laboratory and during the field deployment. During laboratory experiments, spectra (n=15) recorded within a pH measurement cycle had a precision of ±0.0010 pH units (data not shown). Across measurement cycles (n=10) of the same sample, the CHANOS pH channel also achieved a precision (repeatability) of ±0.0010 pH units which is comparable to similar pH sensors. During the three-week field deployment, the precision of the pH measurements was ±0.0019 pH units (n=13) (FIG. 9) over repeated measurements during the last two minutes of a measurement cycle. This standard deviation is slightly larger than that found in the laboratory experiments, which suggests that there may be high variability in water chemistry at the testing site over a short time period. Overall, CHANOS showed good in situ pH repeatability.

Figure 10B:
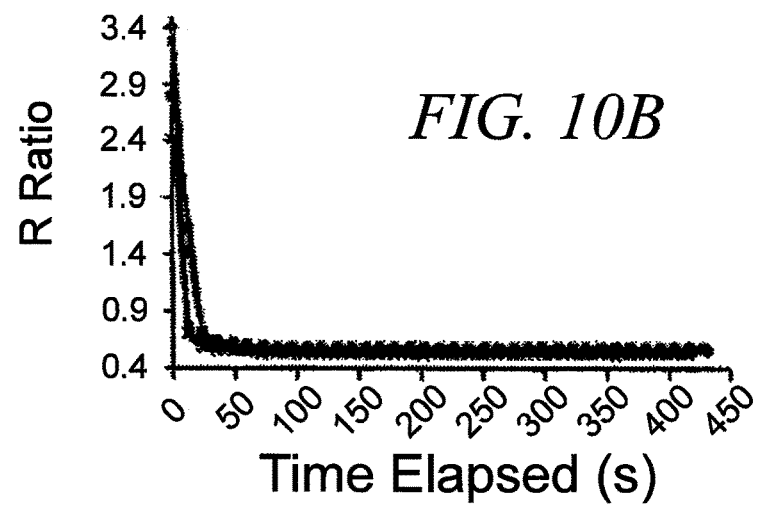
FIG. 10B shows all experimental DIC data with a higher R Ratio scale on the y-axis.
Figure 10A:
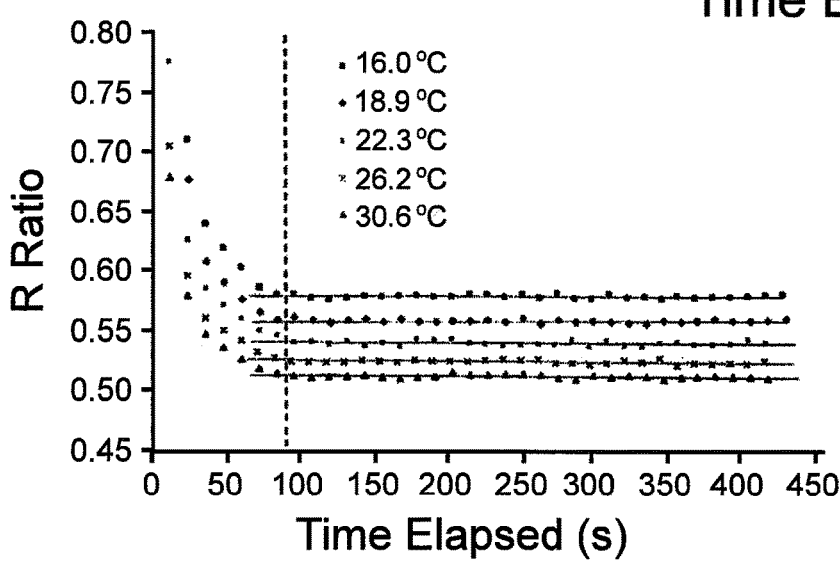
FIG. 10A is a graph of response time of DIC measurements at different temperatures.

The response time for CHANOS DIC measurements was at least 3 times faster than previous spectrophotometric measurements using a similar size of Teflon AF 2400 tubing. At the current settings, it takes ~90 s for fresh processing solution to achieve a stable reading at 100% equilibration for samples with a DIC concentration of ~2000 µmol kg$^{-1}$ (FIGS. 10A and 10B), compared to about 300 s in the previous development. Temperature had an insignificant influence on the response time for the current design based on lab experiments. Such insensitivity is expected as the response time herein reflects the time that it takes for the system to flush the processing solution line with newly $CO_2$ equilibrated solution, which is not temperature dependent.

Currently, CHANOS makes DIC measurements using flow-through, full $CO_2$ equilibration and requires only calibration of a single operation constant B(t) (Eq. 4). The DIC measurement precision is ±2.5 µmol kg$^{-1}$ as determined by repeated measurements, which is similar to previous underway and in situ systems (Table II below).

Figure 11A:
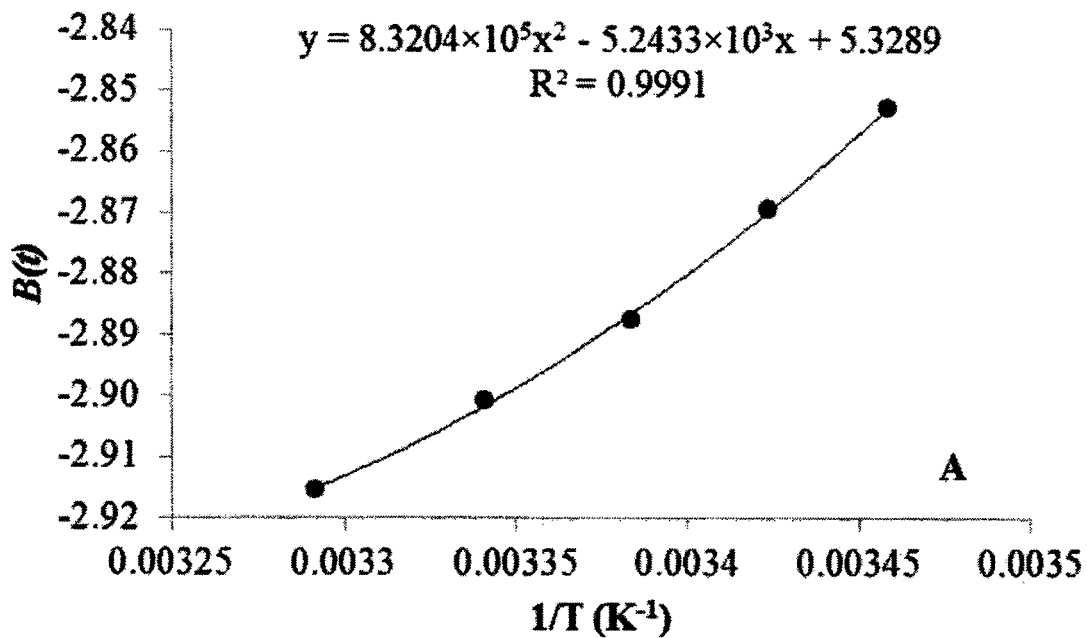
FIGS. 11A and 11B are graphs DIC calibration constant B(t) as a function of measurement temperature under laboratory and in situ conditions, respectively.

Calibration constant B(t) is a function of temperature as described by Eq. 4, where $K_1$, $e_2$, and $K_1'$ of the processing solution are all temperature dependent (FIG. 11A). In theory, B(t) can be calculated using the knowledge of the processing solution composition and thermodynamic constants via Eq. 4. However, the terms in Eq. 4 may have an overall uncertainty that exceeds the acceptable range for climatology-quality DIC measurements. The B(t)-temperature function was thus experimentally determined by measuring CRMs at different temperatures. Such a strategy is convenient as it does not require knowledge of all terms in Eq. 4, but results in well-constrained uncertainties in DIC measurements. The mean difference in B(t) between measured and predicted values based on the best-fit curve in FIG. 11A can be translated to a DIC error of 0.4±2.7 µmol kg$^{-1}$, which is similar to the uncertainty in repeated measurements.

Figure 11B:
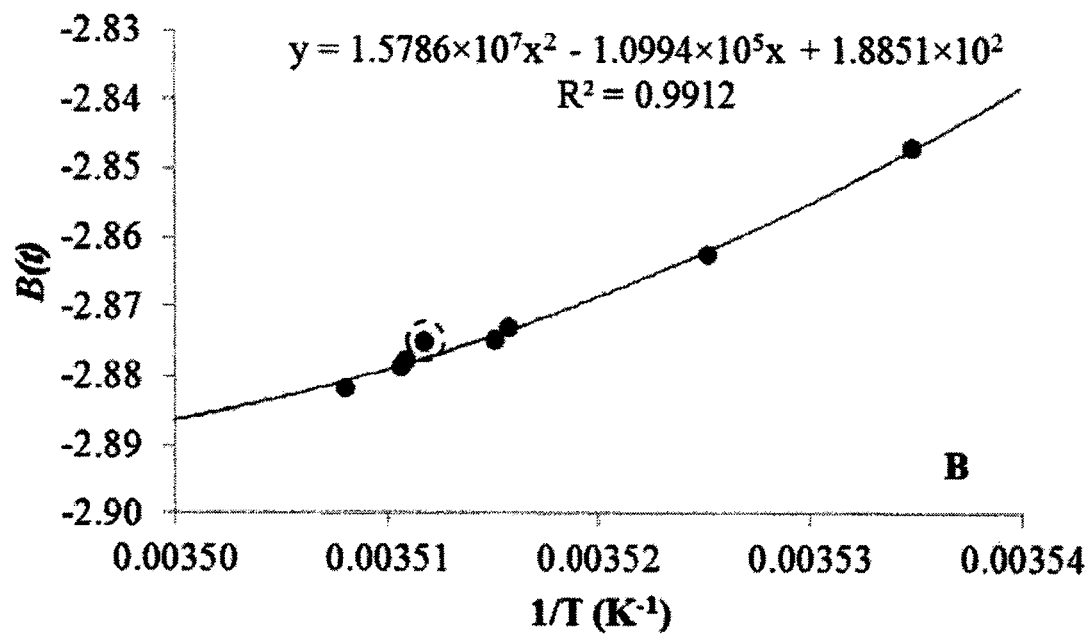

The CHANOS in situ calibration routine using CRMs allows for the determination of the B(t)-temperature function under real deployment conditions. FIG. 11B shows the B(t)-temperature curve obtained during the deployment of CHANOS in November 2013 at the WHOI Iselin dock. The in situ calibration was conducted every 48 to 72 hours. The uncertainty in B(t) relative to the best-fit line in FIG. 11B was equivalent to a DIC error of 0.1±4.9 µmol kg$^{-1}$. The larger uncertainty for the in situ calibration as compared to that obtained under laboratory conditions (FIG. 11A vs. 11B) is largely due to one data point near 1/T of 0.00351 (t=11.6° C.; circled data point in FIG. 11B). Without it, the best-fit curve has a R$^2$ value of 0.9980, equivalent to a DIC error of 1.6±2.7 µmol kg$^{-1}$, comparable to that determined in the lab experiment. The cause of this apparent 'outlier' is unknown. Given the stableness of CRM measurements during the deployment (FIG. 15) and good CRM storage in aluminum bags (FIG. 16), in situ calibration of B(t) should provide a valid means for gauging sensor consistency and performance. The coefficients of the quadratic curves between FIGS. 11A and 11B showed large differences. This might be due to the temperature dependence of the spectrophotometer and the light, which operated at different temperatures in FIGS. 11A (room temperature) and 11B (in situ temperature).

Figure 12A:
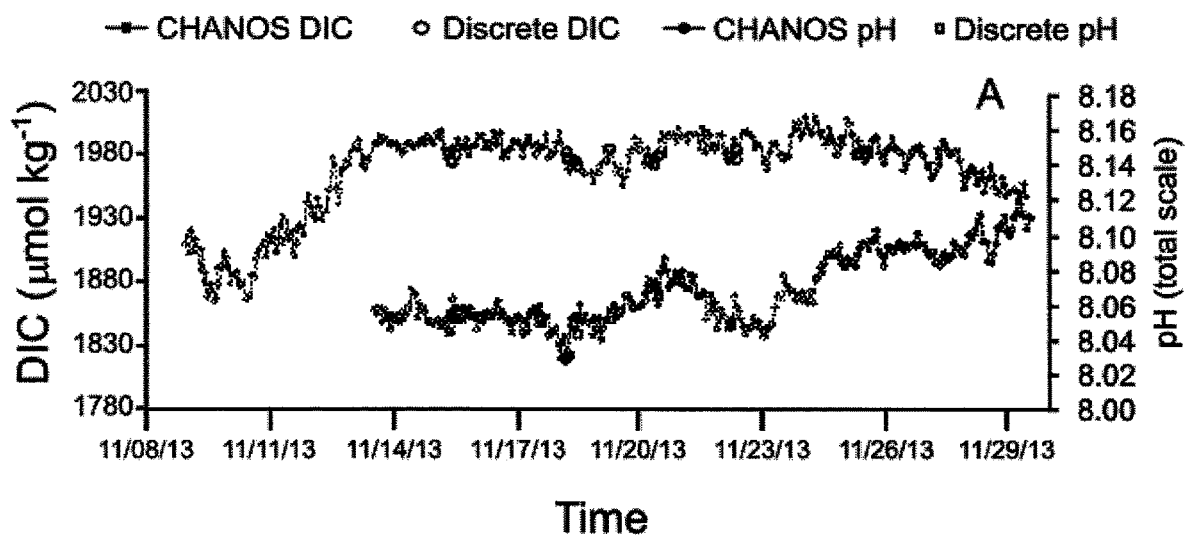
FIG. 12A is a chart of CHANOS and discrete DIC and pH measurements over time.
Figure 12B:
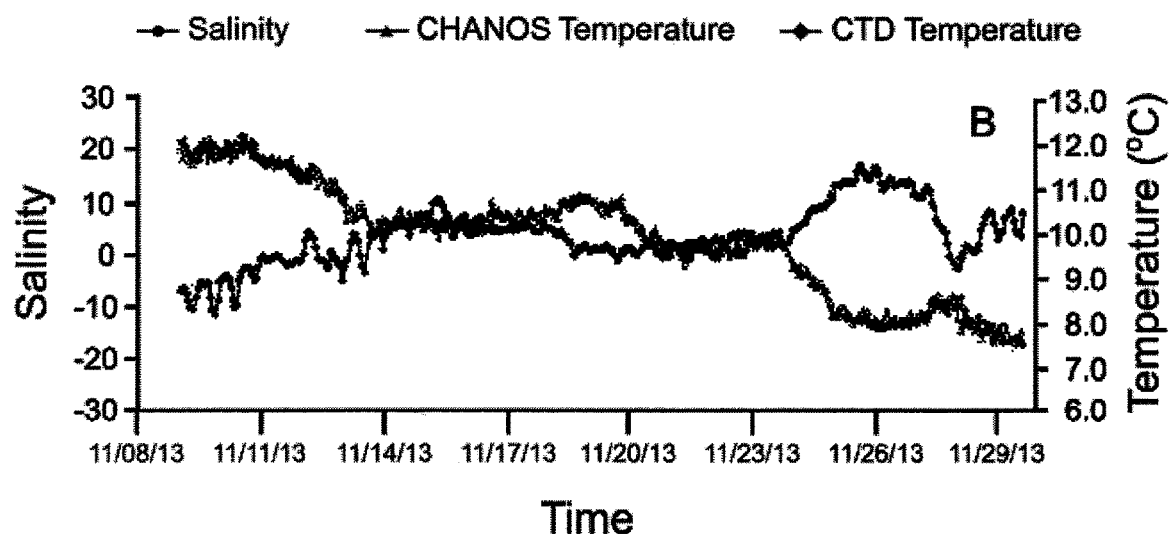
FIG. 12B is a chart of salinity and temperature during the measurement period depicted in FIG. 12A.
Figure 13A:
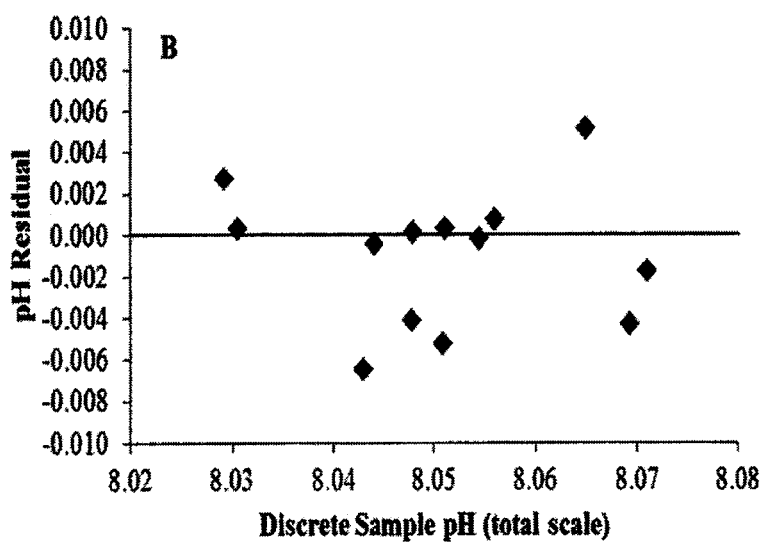
FIGS. 13A and 13B are charts of residuals between CHANOS sensor and bottle measurements over the range of sample DIC and pH, respectively, from FIGS. 12A and 12B.
Figure 13B:
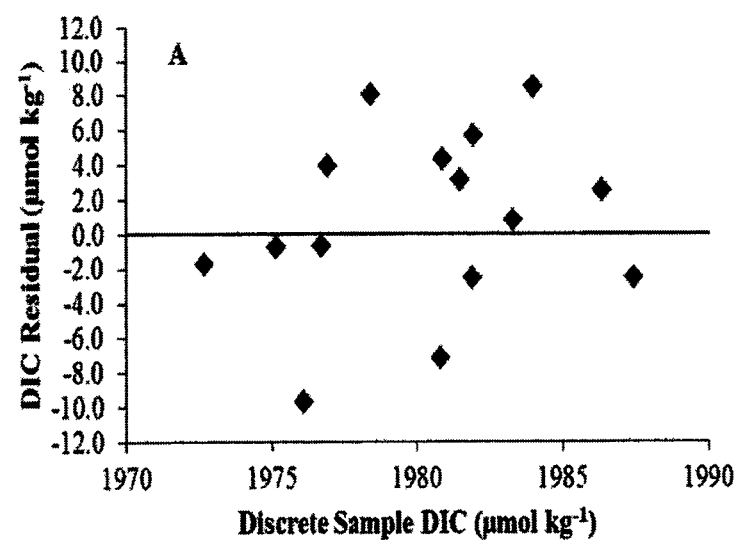

During deployment at the WHOI Iselin dock, CHANOS measurements were directly compared with discrete sample measurements (FIGS. 12A-13B). The DIC channel generated more measurement data than the pH channel because the pH sample pump malfunctioned during the first week of measurement testing. During the deployment, the DIC concentration ranged from 1864 to 2012 µmol kg$^{-1}$, and pH in the total scale (pH$_T$) varied from 8.029 to 8.118 (FIGS. 12A-12B). Meanwhile, salinity only showed a small variation (32.2-32.7), and water temperature exhibited a general cooling trend of ~4.5° C. The diurnal pattern of salinity was often irregular suggesting that the hydrology may not mainly be controlled by the tide. There was a somewhat significant negative correlation between pH$_T$ and temperature (pH$_T$=−0.0147t+8.2046, R$^2$=0.7034, n=320), while DIC was not conservative relative to salinity. These observations suggest that in addition to temperature, biogeochemical processing and physical mixing may also have affected carbonate chemistry at the site.

CHANOS showed good agreement with discrete samples. The mean difference between CHANOS and discrete DIC samples was 0.8±5.2 µmol kg$^{-1}$ (n=15, FIGS. 13A-13B). The mean absolute difference was 4.1±2.9 µmol kg$^{-1}$. Part of this difference may be due to discrete sampling and analytical errors of the DIC bottle samples (~2.0 µmol kg$^{-1}$), and the rest is comparable to the precision of CHANOS (±2.5 µmol kg$^{-1}$). For pH, the mean difference between the sensor and discrete measurements was −0.0010±0.0033 pH units (n=13) with a mean absolute difference of 0.0024±0.0023 pH units (FIG. 8). Such a performance is comparable to existing in situ spectrophotometric sensors (http://www.sunburstsensors.com). Overall, CHANOS achieved the development goal, which was to make climatology-quality, simultaneous, in situ measurements of two primary CO$_2$ parameters—DIC and pH. The deployment data (FIG. 7) also indicate that the new sensor is capable of resolving the high variability of the carbonate system in dynamic environments.

For any continuous measurement, if the response is instantaneous, then continuous detection reflects the true variability of the measured parameter and has the highest spatiotemporal resolution. Otherwise (if response time>0), the measurement reflects a running average of the true variability and has reduced resolution. For shorter response times, the running average better represents the true sample variability. Currently, an estimated ~22 s response time is achieved with the continuous DIC method under partial CO$_2$ equilibration. If such a method is used on a CTD package with a lowering rate of 0.5 m s$^1$ (30 m min$^{-1}$) to make continuous DIC measurements in the water column, each measurement would represent an average concentration over 11 m of water depth (0.5 m s$^{-1}$×22 s); while for the intermittent method with a response time of 5 minutes, the resolution would be 150 m (0.5 m s$^{-1 \times 300}$ s). This represents more than one order of magnitude improvement in spatial resolution.

CO$_2$ fugacity (fCO$_2$) or partial pressure of CO$_2$ (pCO$_2$), which have similar values but slightly different physical definitions, can be measured in situ similarly as DIC. The difference is that the incoming water sample in fCO$_2$ or pCO$_2$ analysis will not be pretreated (e.g. acidifed) as is the case in DIC analysis, so that it is dissolved CO$_2$ in the original sample that is measured. A different indicator for spectrophotometric measurements, or a different reagent for other types of sensor measurements, will be used for fCO$_2$ or pCO$_2$ measurements than that in DIC measurements.

A summary of different configurations within the scope of the present invention, for in situ uses, is provided in the following Table I:

TABLE I

| Technique | Advantages | Disadvantages | Description |
|---|---|---|---|
| Parallel (concurrent) flow with full equilibrium | Less accurate metering pump required, fully continuous measurements, less calibration | Time lag for each recording point with slow travel through equilibration tube, but correctable. | Long flow tube for reagent, parallel flow of sample outside the reagent tube to allow full equilibrium; measurements continuously taken at end of reagent tube. |
| Parallel (concurrent) flow with partial equilibrium | Shorter tubing, less time lag | Accurate metering required for both sample and reagent; more calibration. | Shorter flow tube for reagent, parallel flow of sample outside the reagent tube to allow partial equilibrium; measurements continuously taken at the end of reagent tube. |

TABLE I-continued

| Technique | Advantages | Disadvantages | Description |
|---|---|---|---|
| Countercurrent flow with full equilibrium | Less accurate metering pump required, less calibration | Slow response time; each recording point represents a running average of a previous time interval equivalent to the response time. | Reagent in inner tube and sample in outer tube flow in opposite directions to achieve full equilibrium; measurements taken continuously but represents a running average of a previous time interval equivalent to response time. |
| Countercurrent flow with partial equilibrium | Shorter tubing, fast response time | Accurate metering required only for reagent; more calibration; each recording point. represents a running average of a previous time interval equivalent to the response time. | Reagent in inner tube and sample in outer tube flow in opposite directions to achieve partial equilibrium; measurements taken continuously but represents a running average of a previous time interval equivalent to response time. |

Note that the term "reagent" in Table I above refers to an processing fluid, preferably a liquid, for spectrophotometric sensor measurements. Other types of sensor measurements utilize other reagents as appropriate.

For CHANOS, built-in, in situ DIC calibration has the advantage for remote deployment where discrete sampling and measurements to evaluate sensor performance is difficult. The November 2013 test data suggests that in situ calibration during the deployment is sufficient rather than taking discrete bottle samples to calibrate the system. This includes calibrating the B(t) constant with respect to temperature for all new reagents (FIG. 11B). Storage of CRM and DIC processing solution are also the key to successful deployments. Although not found in this deployment, DIC and TA changes in bagged CRM and changes in TA of DIC processing solutions have occurred in the past. TA of the processing solution and CRM may both change if certain layers of the multi-layered storage bags deteriorate, causing the aluminum layer to come in direct contact with the solution, or if mercury-resistant biological contamination occurs. Changes in solution DIC in bags due to $CO_2$ exchange have been observed less frequently. Improved methods for long-term storage of CRM and processing solutions are being studied. If the storage is robust, in situ calibration will reduce the need for laboratory calibration, which adds convenience for sensor deployment. Alternatively, instead of using CRM, another calibrated processing solution can be used during deployment to cross-check the stability of the primary processing solution and to gauge measurement quality.

The modular design of CHANOS adds flexibility for future development for measurements of other parameters. Because of the similarity between spectrophotometric DIC and $pCO_2$ measurements, with minor modification, $pCO_2$ can be measured with one of the CHANOS channels using a different processing solution (e.g. indicator). The main difference is that the sample will not be pretreated (e.g. acidifed). In alternative constructions, TA could also be measured using an improved method for single-point spectrophotometric titration. In yet other constructions, the sensor makes simultaneous measurements of any combination pair of the four primary carbonate parameters in order to meet a wide range of deployment goals.

A comparison of major characteristics of three DIC in situ sensors is provided in Table II:

TABLE II

| | Robotic Analyzer for the $TCO_2$ System (RATS) [25] | Spectrophotometric Elemental Analysis System DIC (SEAS-DIC) [24] | Channelized Optical System (CHANOS) |
|---|---|---|---|
| Parameters measured with a single system | DIC and pH | DIC | DIC and pH |
| Principle | Conductometric DIC; Spectrophotometric pH | Spectrophotometric | Spectrophotometric |
| $CO_2$ equilibration mechanism for DIC | Static equilibration across silicone rubber | Static equilibration across Teflon AF 2400 tubing | Flow-through equilibration across Teflon AF 2400 tubing |
| Full equilibration time (for a new reagent) | <60 min | ~5 min | ~70 s for DIC; no equilibration for pH |
| Measurement frequency | Hourly | Preparation and initial $CO_2$ equilibration (~9 min in total), one recording per minute afterwards for 50 min; repeat | Preparation (~6 min for DIC and 2 min for pH), continuous flow-through measurements with an interval of every ~12 s for ~6 min for DIC and ~8 min for pH (or longer if larger-volume syringes are |

TABLE II-continued

|  | Robotic Analyzer for the TCO$_2$ System (RATS) [25] | Spectrophotometric Elemental Analysis System DIC (SEAS-DIC) [24] | Channelized Optical System (CHANOS) |
| --- | --- | --- | --- |
|  |  |  | used); repeat (or enter a waiting mode before repeat)*. |
| Precision | ±2.7 µmol kg$^{-1}$; pH not reported | ±2 µmol kg$^{-1}$ | DIC ± 2.5 µmol kg$^{-1}$ pH ± 0.0010 |
| Accuracy (in situ) | ±3.6 µmol kg$^{-1}$; pH not reported | ±2 µmol kg$^{-1}$ | DIC ± 4.1 µmol kg$^{-1}$ pH ± 0.0024 |
| Reported deployment time | 8 weeks | ~8 days | 3 weeks |
| Measurement quality control | Lab and in situ calibration with CRM | Lab calibration with CRM | Lab and in situ calibration with CRM |
| Anti-fouling | Not reported | Copper screening; painting | Copper mesh filtering; external coverage; auxiliary pumping |
| Deployment | Stationary; Submerged to at least 1,000 m | Stationary; Submerged to maximum of 250 m | Mobile or stationary; Land, water surface, or underwater (up to 3,000 m or more) |

*Reference can be taken less frequently (e.g. only once per hour) to shorten preparation steps and to capture a higher measurement frequency.

In one construction, the $CO_2$ equilibration cell (FIG. 1B) in the DIC J-box is coiled (FIG. 2B) and consists of a ~120 cm long piece of Teflon AF 2400 tubing (0.04 cm ID by 0.05 cm OD.; Random Technologies, LLC) inserted in a PEEK tubing (0.10 cm ID by 0.16 cm OD; Upchurch Scientific). A custom-made piece of PEEK tubing was used to seal the solution inside the Teflon tubing from the sample at the seawater entry and exit positions. The DIC and pH measurement cells, FIGS. 2B-2C, consist of a 1 cm Z-Cell (SMA-Z-10, FIAlab Instruments, Inc) and a custom-made 10 cm PEEK rod with a 3 mm throughout borehole, respectively. The J-boxes are oil filled for pressure compensation and protection. They are connected to the other components of the sensor through tubing (for reagents and sample water), optical fibers (to light sources and spectrophotometers), and electronic cables (not shown). Two thermistors are built into each J-box to monitor sample temperature during measurements.

For the DIC channel, the components enclosed in the pressure housing include a controller board for the syringe pump stepper motors, an AD converter for reading thermistors, a power control board which sequences all of the valves and pumps during measurement operation, and a TERN 186FN microprocessor for sequencing the whole system and collecting the data. An Ocean Optics USB 4000 spectrophotometer with a serial port reads the data. Custom-made optical fibers connect the spectrophotometer to the optical Z-cell in the DIC J-box. A broadband LED source (Rebel Star, Luxeon Star LEDs) or other suitable light source is connected to the measurement cell through the fibers as well. This array of equipment is duplicated to form a separate pH system, except for the pH measurement cell 412, which sits outside of the J-box (FIG. 2D). The system runs on 24V DC power either through an external source or through a rechargeable battery pack. Controlling software, written in C, includes routines to read the spectrophotometer and either store the data on an internal compact flash card or transfer it to a shore computer. The system is driven by user-configured parameter sequences, which can be issued by a program on a shore server, or alternatively, can be read from a compact flash card for autonomous operation.

Four custom-made syringe pumps or other precise volumetric pumps are contained in Delrin housings and filled with pressure-balanced oil (e.g., Royal Purple #7, hydraulic oil, or other suitable oils). Each stepper motor drives a lead screw with a shaft seal, which mechanically pushes the plunger of a syringe up to 6.4 cm. Three 3 mL and one 1 mL syringes are currently used in the system. They are able to precisely deliver solution with an overall uncertainty of 2-5 µL at the rates used.

FIGS. 14A-14B summarize the operation steps of a measurement cycle for CHANOS analytic channels for DIC and pH, respectively, during the three-week field deployment. Continuous measurements within each measurement cycle (currently 6 minutes for DIC and 8 minutes for pH) can be made for a longer period of time if larger processing solution and acid syringes are used. The operation steps can also be customized to achieve higher or lower resolutions of measurements to fulfill different deployment purposes. For example, the running sequence can be modified so that reference is taken less frequently and the measurement interval is longer (e.g., 2 min as compared to ~12 s), in order to save solutions and extend the measurement duration within one measurement cycle.

DIC discrete samples were measured using a DIC autoanalyzer (AS-C3, Apollo SciTech) which uses a non-dispersive infrared $CO_2$ analyzer (LiCOR 7000) for detection. This instrument has a precision and accuracy of ±2 µmol kg$^{-1}$. Discrete pH samples were measured at 25° C. based on the conventional spectrophotometric procedure using m-cresol purple on a HP 8453 spectrophotometer. Processing solution perturbation and impurity were corrected. The pH measurements have a precision of ±0.0004 pH units and an accuracy of 0.001-0.002 pH units. The pH at in situ temperature was calculated by using bottle DIC and pH at 25° C. The addition of mercuric chloride to pH samples of local coastal waters did not differ from those that were not poisoned.

Figure 15:
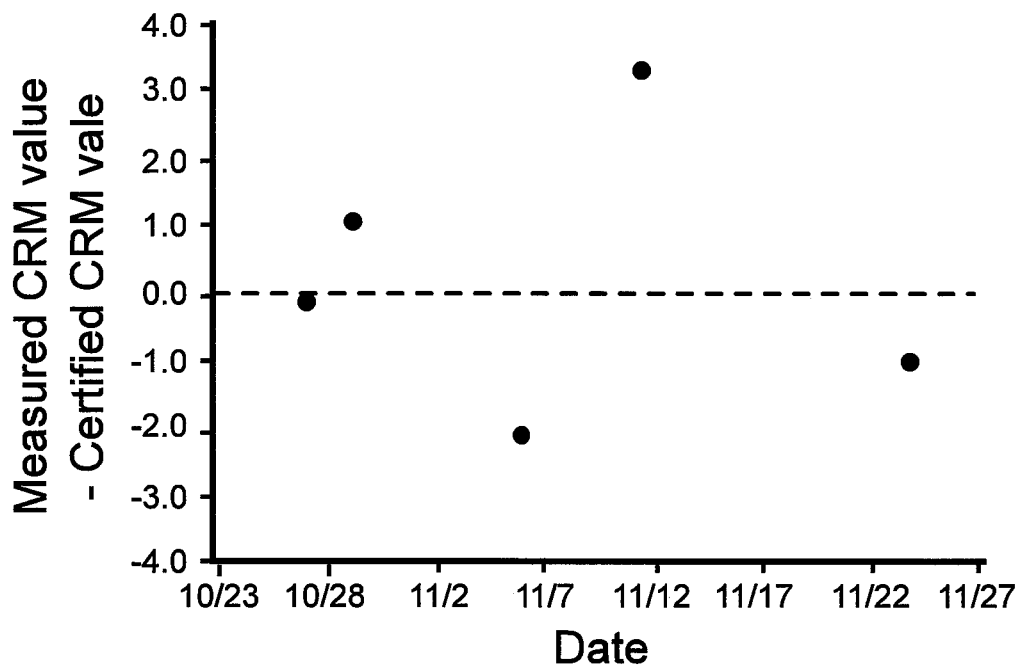
FIG. 15 is a chart comparing between measured Certified Reference Material (CRM) values by CHANOS and certified CRM values over a three-week period.
Figure 16:
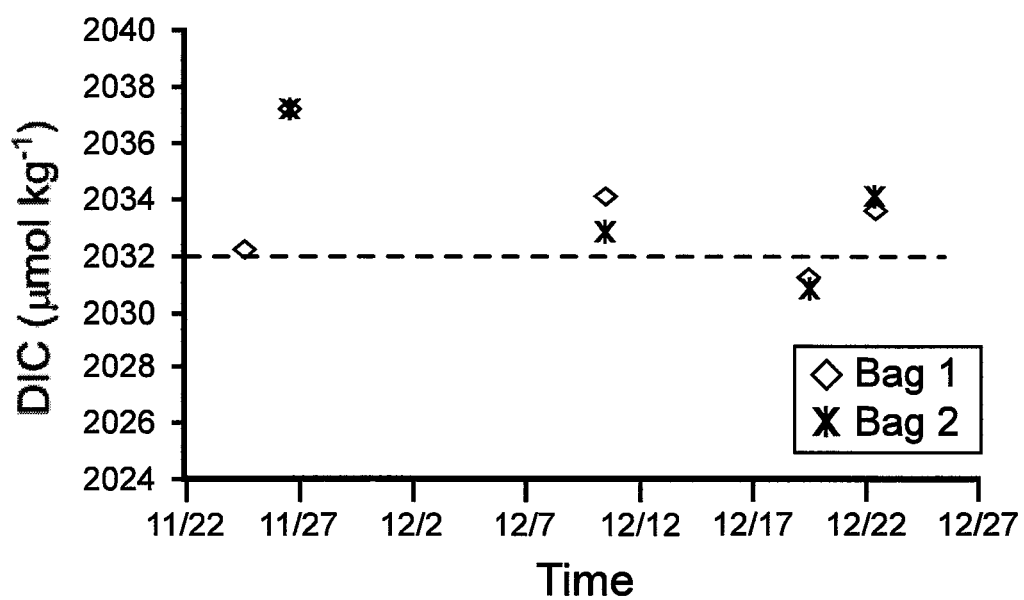
FIG. 16 is a chart comparing measurements of two laminated aluminum bags of CRM over time.

FIG. 15 shows that over the three-week period of the field deployment, the measurements of a bagged CRM (Batch #131) by the CHANOS DIC channel were within 0.3±2.1 µmol kg$^{-1}$ of the certified CRM value. These CHANOS measurements are not included in the B(t) calibration (FIG. 11B). Such results indicate that bagged CRM and processing solution did not show detectible changes in their DIC and TA concentrations during the deployment.

A laboratory experiment was also conducted to test the difference in DIC concentrations between two bags of CRM and to assess their stability over a four-week period (FIG.

16). Comparison between measurements of two laminated aluminum bags of CRM during the period of Nov. 24 and Dec. 22, 2014. CRM Batch #137 (DIC=2031.9 µmol kg$^{-1}$, S=33.607) was used for the test. The dash line denotes the certified CRM value. Because of instrument issues, the data from Bag 2 on Nov. 24, 2014 is not shown. DIC samples were directly collected from the bags into glass syringes for measurements. The measurements were made using an Apollo DIC auto-analyzer (AS-C3). The mean difference in DIC concentration between the two CRM bags was 0.3±0.8 µmol kg$^{-1}$ (n=4) during the four-week period. The mean difference between the measured and the certified value was 1.7±2.3 µmol kg$^{-1}$ (n=5) for Bag 1 and 1.8±2.6 µmol kg$^{-1}$ (n=4) for Bag 2. These comparison metrics indicate that 1) changes in DIC when transferring the CRM to different bags should be limited through careful operation; 2) CRM stored in aluminum bags should be reasonably stable over a month-long period.

Dissolved Analyte Channels

The instant invention described herein also provides the ability to simultaneously measure additional analytes in real time by adding or exchanging analyte channels. In the preferred embodiments, the device comprises at least two J-boxes, and one or more J-boxes are reversibly attached such that a user can selectively affix a J-box containing a desired channel. The sensor or sensor systems inside a J-box are referred to generically as channels. As described above, one channel is for measuring dissolved gases, particularly DIC. Another channel is for precise pH measurement. Additional channels now described, including channels for dissolved metal ions, and alkalinity.

A method for spectrophotometric determination of dissolved silver is described by Wen et al. Spectrochimica Acta Part A Molecular and Biomolecular Spectroscopy 97, page 782-7, 2012, and incorporated by reference herein. The instant invention provides for an autonomous, long-term, and real-time measurement system for dissolved metals. In one embodiment, a dissolved metal channel (METNOS) comprises a liquid-liquid extraction, and a spectrophotometric-based analysis system, as illustrated in FIG. 17. Inlet port 1704 allows sample fluid 1708 into the channel and joins with valve 1712, which allows for mixing of sample fluid with at least one pretreatment fluid from at least pretreatment reservoirs 1714 and 1715 by means of valve 1717 and pump 1716.

In some MENTOS embodiments, a first pretreatment fluid comprises a dispersive extraction solvent. Addition of this solvent to the sample fluid forms a cloudy solution, and the analyte of interest (e.g. dissolved metals) are purified or micro-extracted away from the remaining solution in the sample processing cell 1760, resulting in sedimentation of the analyte. In the preferred MENTOS embodiment, the first pretreatment fluid comprises a dithizone-chloroform solution. The remaining sample liquid remains under flow and is discarded as waste 1710 out of port 1706.

The purified dissolved analyte may be re-suspended by a second pretreatment fluid from reservoir 1715, which is then mixed in the processing cell 1760 with processing liquid from processing solution reservoir 1736 by pump 1738, and directed to the measurement cell Z by liquid feed 1720. In the preferred MENTOS embodiment, the second pretreatment fluid may be methanol, ethanol, acetone, acetonitrile, and ethyl acetate, or a combination thereof. Spectrophotometric analysis is performed with light source L in measurement cell Z and measured by measurement device 1745 (e.g. a spectrophotometer). Analyzed samples are discarded to waste 1730 through pressure housing 1702.

Alternative MENTOS embodiments include a sample processing cell that further comprises an emulsification mechanism, which utilize an apparatus to assist in the extraction processes without the need for pretreatment fluids. In other embodiments, the emulsification mechanism may be in place of, or in addition to the use of a pretreatment fluid. In some embodiments, the emulsification mechanism comprises an ultrasound generator.

Similarly to the above described channels, the MENTOS channel provides for reference measurement via reference reservoir 1764, pump 1766, valve 1722 and conduit 1723. Additional pretreatment reservoirs may be incorporated into the system. It is to be understood that valve 1717 before pretreatment reservoirs may be modified to accept additional pretreatment reservoirs. Valve 1717 is interconnected to and controlled by the controller and such a system is configured to measure different dissolved metals, with different pretreatment solutions (e.g. different metal chelators and extractants). One example of additional pretreatment regents include the copper chelator bathocuproine disulfonate. The pH of the sample solution may further be adjusted by buffering one or more pretreatment solutions, for example including a buffer to adjust the final solution to a pH within 2.0 to 11, depending on the analyte to be measured.

Additional Analyte Channels

Another channel provided by the instant invention is the total alkalinity channel (ALEKTOS). Total alkalinity (TA) is a measure of the buffering capacity of a fluid body, defined as the moles of hydrogen ion equivalents to the excess of proton acceptors over proton donors in one kilogram of fluid. TA is useful for understanding physical and biogeochemical processes in the ocean, for example, anthropogenic CO2, shell-building organism calcification, the state (dissolution or precipitation) of calcium carbonate minerals, the ratio of aerobic to anaerobic respiration and water mixing. As stated above, TA can be used with another parameter (pH, pCO2 or DIC) to characterize the carbonic system.

Figure 18:
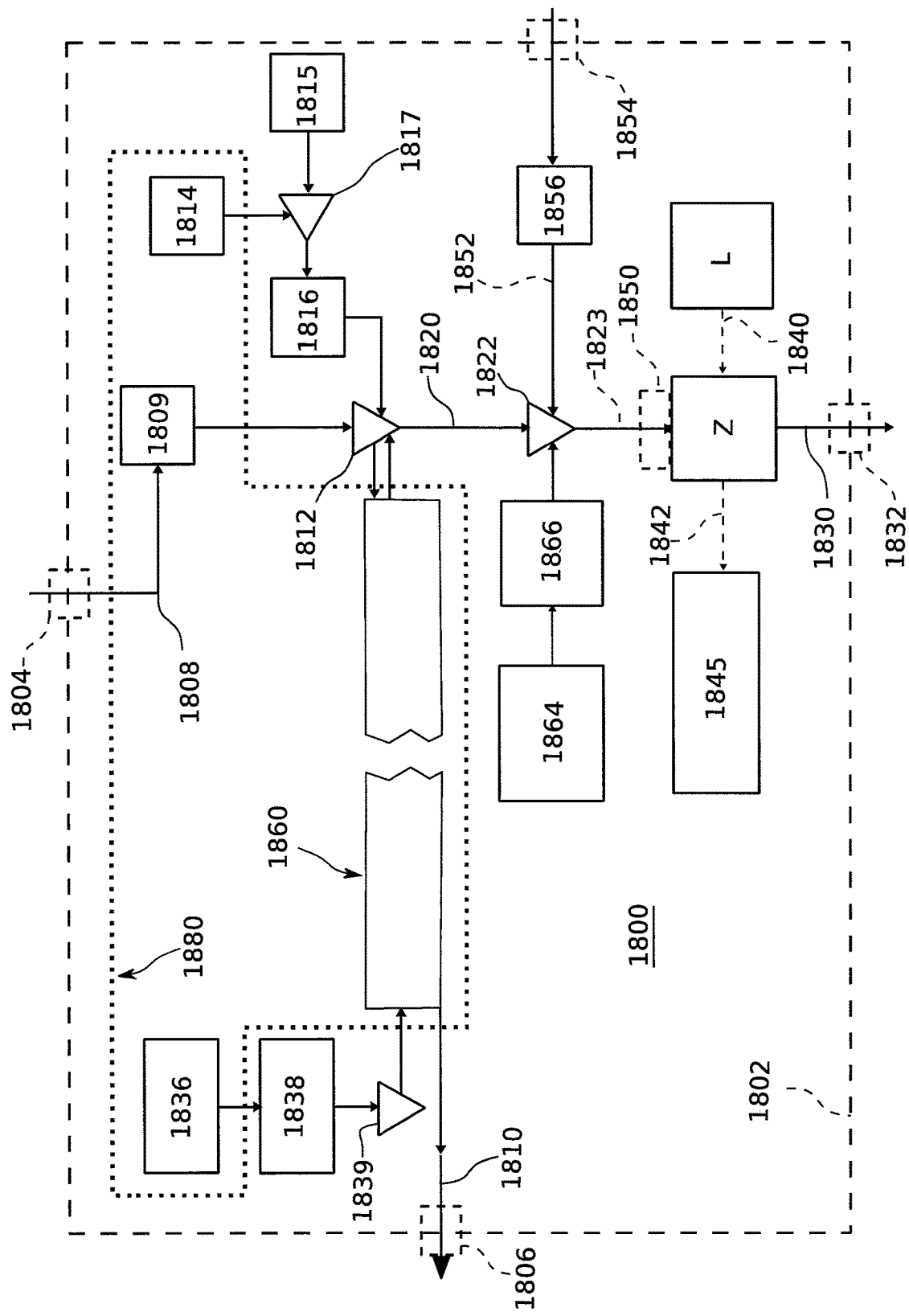
FIG. 18 is a schematic block diagram of an ALEKTOS channel according to the present invention.

Seawater titration and TA measurement has been previously performed with stationary, maintained devices, as described in more detail in Li et al., Environmental Science & Technology, vol. 47, no. 19, 2013, pp. 11139-11146, and incorporated by reference herein. The present ALEKTOS channel provides a long term, autonomous, mobile and submersible system for the measurement of real-time TA as the device moves through a body of water. As depicted in FIG. 18, the ALEKTOS channel 1800, has many components similar to other channels described herein. Components having the same or very similar function to other channels have the same base reference numbers but are listed in the 1800 s, for example sample fluid 1808 corresponds to sample fluid 1708 and 108 and sample fluid pump 1810 correlates to pump 1710 and 110 and so on.

Important features of the ALEKTOS channel include the pretreatment reservoirs 1814 and 1815, connected to the sample line 1808 by means of valve 1817, pump 1816 and valve 1812. Most often the pretreatment fluid includes a titrant fluid comprising an acid mixed with an indicator. In some embodiments titrant and indicator are separated into reservoirs 1814 and 1815 and mixed just before combination with the sample. In the preferred embodiment, the pretreatment fluid is HCl (titrant) and bromocresol green (indicator). Valve 1812 preferably comprises an 8-way valve, for example a C22Z-6188EH valve from Valco Instruments, Houston, Tex. Valve 1812 is controlled by the controller and switches the device between modes, of at least sample-titrant flushing mode (referred to as flushing mode) and sample-titrant mixing-reaction mode (referred to as mixing mode).

Flushing mode includes at least one of the sample or the titrant are flushed through the system, to remove previous samples from the system. Sample is pumped through line 1808, pump 1809, valve 1812 and either (i) through processing cell 1860, then through measurement cell Z and out of the system by line 1820, 1823, 1830 and port 1832, or (ii) directly from valve 1812 to line 1820 without passing through the sample processing cell 1860. Likewise, titrant may be flushed from at least one reservoir 1814 and 1815, and by pump 1816. Titrant flushing out of the system is accomplished as above for sample flushing in options (i) and (ii).

In the mixing mode, valve 1812 creates a reaction loop that is mixed by the sample pump 1809 and pump 1816, which mixes titrant and sample at a constant volume ratio, where the amount of titrant is always more than enough to titrate the sample or reference fluid. In the preferred embodiment, pump 1809 is a modified peristaltic pump (WX10, Baoding Longer Precision Pump Co) and pump 1816 is a solenoid pump from Chem Fluidics, typically delivering 50 µL per pulse. Pump 1809 modifications comprise of adding a magnet to the rotor and a hall sensor of the housing. A magnetic signal is produced when the magnet passes the sensor, stopping the pump and thus achieving a constant internal volume.

The sample processing cell 1860 in the ALEKTOS embodiment is adapted to further modify the pretreated sample fluid. In the preferred embodiment, the processing cell removes CO2 from (pretreated) sample fluid. This is accomplished in a similar fashion as the CHANOS channel described above. A two-conduit system is employed where a first conduit forms the path for the mixed pretreated sample (e.g. titrant and sample or titrant and reference) by a selectively-permeable membrane, most often Telfon AF2400. In the preferred embodiment, the selectively-permeable membrane allows for the transfer of CO2 from the sample to the processing fluid, however, the instant invention allows for embodiments that transfer other substances (e.g. Nitrogen gas, or molecules below a specific molecular weight).

The second conduit envelops the first and accepts a processing liquid. The processing liquid has a stationary, concurrent or countercurrent flow, with respect to the pretreated sample. A stationary relationship refers to a system where the processing liquid is unmoving while the pretreated sample moves through the processing cell 1860. The selectively-permeable membrane of the processing cell allows for at least partial equilibrium between the pretreated sample and the processing fluid. In some embodiments the flow is determined by the construction, in others, and illustrated in FIG. 18, processing liquid flow originates from reservoir 1836, is moved by pump 1338 and flow direction is dictated by valves 1812 and 1839. Processing liquid may comprise any suitable fluid for modifying the pretreated sample (e.g. removing a dissolved gas or gasses). In the currently preferred embodiment, the remover liquid comprises 1 M NaOH, which removes dissolved CO2 from the pretreated sample.

After passage through the processing cell, the mixed and modified sample is referred to as a processed sample, and is measured for the desired analyte (e.g. total alkalinity) at the measurement cell Z. A light source L (e.g. a LED array), illuminates the measurement cell Z, and reacts with the processing solution to measure pH, and therefore TA of the sample by measuring device 1745 (e.g. a spectrophotometer). In the currently preferred embodiment, the light source L has a filtering mechanism of two optical filters with central wavelengths of 443.8 and 615.8 nm and half bandwidth of 6.7 and 7.4 nm, respectively. The filtering mechanism enables a narrow bandwidth light, resulting in accurate spectrometric measurement. The measuring device 1745 may be any measuring system as known in the art; in the currently preferred embodiment, measuring device 1745 is a spectrophotometer.

The instant invention further provides a means to select the desired fluid for measuring an analyte. It can be appreciated that in some embodiments (e.g. CHANOS), that the analyte to be tested permeates across the selectively-permeable wall (e.g. Teflon AF 2400 tubing) from the first conduit 12 to reside in the at least partially equilibrated processing fluid of second conduit 14. The solution from second conduit 14 is then directed to the measurement cell Z. In other embodiments, the analyte is retained in the first conduit 12, while undesired molecules or substances are removed by the selectively-permeable (and analyte-resistant) wall. In these embodiments, the first conduit is directed to the measurement cell Z. In some embodiments, it is desirable to change the analyte to be measured, and without changing the physical design of the embodiment, the conduit that is to be directed to the measurement cell. Therefore, a switching mechanism is provided to change which fluid is sent to the measurement cell. Switching mechanism 162 is depicted in FIG. 2A, but may be incorporated into any embodiment described herein. In the preferred embodiment, switching mechanism 162 comprises a valve accepting input from the first and second conduits and outputs to flow 120 and waste 110.

Bubble control, and the elimination of bubbles from the system, and in particular, the measurement cell is a key aspect of the present invention. The instant invention provides a bubble control mechanism 1850, which may comprise one or more of several means. In one embodiment, the measurement cell Z is cross-shaped, with an internal volume of ~1.3 mL and an optical path length of ~1 cm and made of Plexiglas. The optical path and the flow path of the measurement cell Z are perpendicular to each other ("cross-shaped"). When the cell is positioned with light path horizontally and flow path vertically, the bubbles in the cell float and leave the optical path free of bubbles. In addition, the relatively large internal volume of the cell allows the seawater and titrant to mix rapidly.

In some situations, the system may not be situated in an orientation to allow for efficient removal of bubbles by simple floatation (e.g. when the system is towed behind a vessel). Therefore, in some embodiments, the bubble control mechanism further comprises a flushing mechanism. The flush may be provided by one of the pumps described herein, set its maximum capacity, or near maximum to flush any bubbles out of the measurement cell Z along with sample, typically untreated sample. In other embodiments, the flush is provided by a separate line 1850, connected to the measurement cell Z by pump 1852 and valve 1822. The line 1850 may accept fluid from the external environment, by a separate opening port 1854 or by port 1804, or to an optional reservoir 1856. This reservoir may be filled with a fluid adapted to efficiently flush bubbles out of the measurement cell, anti-fouling fluid, or any other suitable fluid.

In another embodiment, the bubble control mechanism comprises the regulation of the sample flow rate or the sample aspiration rate. In another embodiment, the bubble control mechanism 1850 comprises an aspirator before the optical cell, able to take up bubble-containing fluid and remove it from the device entirely or shunt it around measurement cell Z. In a further embodiment, a modified vacuum aspirator is utilized to generate a vacuum while the device is in motion, or otherwise rocking. The vacuum draws dissolved air from the sample after uptake by the device and thus reducing the likelihood of bubble formation. Still further embodiments are adapted for all dissolved gases to be removed in the sample processing cell 1860, and a vacuum aspirator may be incorporated therein as well. Finally, in some embodiments, the bubble control mechanism comprises a rocker or shaker means, such as a magnetic stir bar, to prevent bubbles from attaching to surfaces of the measurement cell Z.

The temperature of the ALEKTOS channel is very important. Previously known stationary systems rely on incubating the fluid containers (e.g. titrant and sample) in temperature-controlled water baths. Such a solution is not possible in the self-contained, autonomous ALEKTOS system. To achieve precise temperature control, the instant invention further provides a temperature control mechanism. The temperature control mechanism 1880 keeps the system at a stable temperature, preferably $25.0\pm0.1°$ C. In some embodiments, the temperature control is incorporated into the housing 1802. In other embodiments, the temperature control mechanism incorporates only a subset of components (FIG. 18 dotted area 1880). In the currently preferred embodiment, at least the sample 1808, titrant reservoir 1814, processing cell 1860, processing fluid reservoir 1836, and associated feed lines are all temperature controlled by the temperature control mechanism. In other embodiments, the temperature control mechanism may encompass less components of the system. In still further embodiments, the temperature control mechanism may encompass additional components.

In one embodiment, the temperature control mechanism comprises a Peltier Controller heat pump. In some embodiments, the temperature control mechanism comprises a joule heater. In other embodiments, it comprises a microwave-based heater.

The ALEKTOS channel is utilized by activating the temperature control mechanism and allowing the encompassed components to come to the desired temperature (e.g. 25° C.). The system is put into flushing mode by the controller, to flush out any unwanted fluid, or a previous sample from the flow lines. A reference measurement can be taken before measuring a sample. Reference fluid in reservoir 1864 is pumped into measurement cell Z by pump 1866. In addition, a background light intensity can be taken after flushing when no processing solution or reference fluid is in measurement cell Z. One measurement preferably comprises of multiple light detections, often 10 to 20 detections are taken to ensure a stable measurement signal. After stable measurement, the last detection, or an average of a portion of the last detections, preferable an average of 2-10 detections, is sent to the controller as output.

The sample measurement commences after reference measurement. Sample and pretreatment (e.g. titrant) are mixed and processed in sample processing cell 1860. For TA measurements, sample processing comprises the removal of one or more gases (e.g. carbon dioxide gas). For sample processing the system may be directed with either concurrent, countercurrent or stationary flow of processing fluid to sample fluid, respectively. The mixed sample is then passed through the measurement cell Z, measured and removed from the system by port 1832. Measurement for the sample in the same manner as for the reference, except that the sample may be run continuously through a range of pH values (i.e. the sample is titrated with acid).

Although specific features of the present invention are shown in some drawings and not in others, this is for convenience only, as each feature may be combined with any or all of the other features in accordance with the invention. While there have been shown, described, and pointed out fundamental novel features of the invention as applied to one or more preferred embodiments thereof, it will be understood that various omissions, substitutions, and changes in the form and details of the devices illustrated, and in their operation, may be made by those skilled in the art without departing from the spirit and scope of the invention. For example, non-cylindrical passages such as baffles or other dividers can be utilized between the concurrent or countercurrent flows of the reagent and sample fluids. It is expressly intended that all combinations of those elements and/or steps that perform substantially the same function, in substantially the same way, to achieve the same results be within the scope of the invention. Substitutions of elements from one described embodiment to another are also fully intended and contemplated. It is also to be understood that the drawings are not necessarily drawn to scale, but that they are merely conceptual in nature.

It is the intention, therefore, to be limited only as indicated by the scope of the claims appended hereto. Other embodiments will occur to those skilled in the art and are within the following claims.

What is claimed is:

1. A system for continuously measuring a concentration of at least one pre-selected dissolved analyte in a first sample water obtained from a quantity of water, comprising:
    a first processing cell having at least a first conduit defining a first passage with at least one selectively-permeable wall configured to pass at least the at least one pre-selected dissolved analyte through the at least one selectively-permeable wall into a processing liquid directed continuously through the first conduit, the at least one selectively-permeable wall resisting flow of a portion of the first sample water therethrough, the at least one selectively-permeable wall extending along a second conduit defining a second passage through which the first sample water is conducted, and the at least one selectively-permeable wall being in contact with the first sample water in the second conduit;
    at least one pump to direct processing liquid continuously through the first conduit while continuously moving the first sample water and the processing liquid relative to each other in a countercurrent flow relationship while being separated from one another via the at least one selectively-permeable wall to generate a first at least partially equilibrated processing liquid and a processed sample;
    at least one detector; and
    at least one guide (i) operatively connected to the at least one detector and the first processing cell and (ii) configured to transmit electromagnetic energy to the at least one detector from the first processing cell;
    wherein the at least one detector utilizes the electromagnetic energy transmitted from the first processing cell to measure the concentration of the at least one pre-selected dissolved analyte.

2. The system of claim 1 further comprising a pretreatment mechanism comprising:
    at least one pretreatment liquid residing in at least one pretreatment reservoir;
    at least one pump; and
    at least one valve;
    wherein the at least one pretreatment reservoir is connected to the at least one pump and the at least one valve; and wherein the at least one pump directs pretreatment liquid to the at least one valve, the at least one valve connected to the first processing cell and configured to pass pretreatment liquid to the first processing cell.

3. The system of claim 2 further comprising a microprocessor programmed to sequence the system to perform continuous measurements.

4. The system of claim 1 wherein the at least one pre-selected dissolved analyte passes through the at least one selectively-permeable wall and into the at least partially equilibrated processing liquid, and the at least one detector measures the at least partially equilibrated processing liquid obtained from the first conduit.

5. The system of claim 1 wherein the at least one pre-selected dissolved analyte is retained in the portion of the first sample water that does not pass through the at least one selectively-permeable wall, and the at least one detector measures the processed sample obtained from the second conduit.

6. The system of claim 1, further comprising:
a second water sample having at least a second pre-selected dissolved analyte having a concentration in the second water sample;
a second processing cell having at least a third conduit defining a third passage with at least a second selectively-permeable wall configured to pass at least the second pre-selected dissolved analyte through the second selectively-permeable wall into a second processing liquid, the second selectively-permeable wall resisting flow of at least a portion of the second water sample therethrough, the second selectively-permeable wall extending along a fourth conduit defining a fourth passage through which the second water sample is conducted, and the second selectively-permeable wall being in contact with the second water sample in the fourth conduit;
at least a second pump, to direct the second processing liquid continuously through the third conduit while continuously moving the second water sample and the second processing liquid relative to each other while being separated from one another via the second selectively-permeable wall to generate a second at least partially equilibrated processing liquid and a second processed sample; and
wherein the at least one detector is separated from the first and second processing cells and measures the concentration of the at least one pre-selected dissolved analyte and the second pre-selected dissolved analyte, the at least one pre-selected dissolved analyte being measured from a homogenous portion of either the first at least partially equilibrated processing liquid and the processed sample, and the second pre-selected dissolved analyte being measured from a homogenous portion of either the second at least partially equilibrated processing liquid and the second processed sample.

7. The system of claim 1 wherein the first sample water is configured to be obtained continuously by the system from the quantity of water.

8. The system of claim 1 wherein the at least one detector uses spectrophotometric measurement, utilizing a flow-through optical cell.

9. The system of claim 1 further comprising a device for measuring pH of the first sample water.

10. The system of claim 1 wherein the system is configured for installation and use on at least one of an Autonomous Underwater Vehicle, a Remotely Operated Vehicle, a mobile surface platform, a mobile underwater platform, a stationary surface platform, or a stationary underwater platform.

11. The system of claim 1 wherein the at least one pre-selected dissolved analyte is selected from at least one of dissolved inorganic carbon, carbon dioxide, oxygen, ammonia, dissolved nitrogen gas, total alkalinity, or a dissolved metal ion.

12. The system of claim 1 further comprising a bubble control mechanism configured to eliminate bubbles in the at least one detector.

13. The system of claim 1 further comprising a microprocessor programmed to (a) direct the at least one pump to move at least the processing liquid continuously through the first conduit and (b) sequence the system to perform continuous measurements while the at least one pump directs processing liquid continuously through the first conduit and while the first sample water moves continuously through the second conduit.

14. A method for continuously measuring a concentration of at least one pre-selected dissolved analyte in a first sample water obtained from a quantity of water during a selected time period, comprising:
selecting a first processing cell having at least a first conduit defining a first passage with at least one selectively-permeable wall configured to pass at least the at least one pre-selected dissolved analyte through the at least one selectively-permeable wall into a processing liquid, the at least one selectively-permeable wall resisting flow of a portion of the first sample water therethrough, the at least one selectively-permeable wall extending along a second conduit defining a second passage through which the first sample water is conducted, and the at least one selectively-permeable wall being in contact with the first sample water in the second conduit;
continuously directing processing liquid through the first conduit while continuously moving the first sample water and the processing liquid relative to each other in one of a concurrent and a countercurrent flow relationship while being separated from one another via the at least one selectively permeable wall to generate a first at least partially equilibrated processing liquid and a processed sample; and
measuring, utilizing at least one detector, the concentration of the at least one pre-selected dissolved analyte in a homogenous portion of one of either the first at least partially equilibrated processing liquid obtained from the first conduit and the processed sample obtained from the second conduit, wherein at least one guide is (i) operatively connected to the at least one detector and the first processing cell and (ii) configured to transmit electromagnetic energy to the at least one detector from the first processing cell, wherein the at least one detector utilizes the transmitted electromagnetic energy to measure the concentration of the at least one pre-selected dissolved analyte, and wherein the processing liquid and the first sample water are moved continuously through the first processing cell during measurement.

15. The method of claim 14 wherein the at least one pre-selected dissolved analyte passes through the at least one selectively-permeable wall and into the at least partially equilibrated processing liquid, and the at least one detector measures the at least partially equilibrated processing liquid obtained from the first conduit.

16. The method of claim 14 wherein the at least one pre-selected dissolved analyte is retained in the portion of the first sample water that does not pass through the at least one selectively-permeable wall, and the at least one detector measures the processed sample obtained from the second conduit.

17. The method of claim 14 further comprising:
obtaining a second water sample having at least a second pre-selected dissolved analyte having a concentration in the second water sample;
selecting a second processing cell having at least a third conduit defining a third passage with at least a second selectively-permeable wall configured to pass at least the second pre-selected dissolved analyte through the second selectively-permeable wall into a second processing liquid, the second selectively-permeable wall resisting flow of at least a portion of the second water sample therethrough, the second selectively-permeable wall extending along a fourth conduit defining a fourth passage through which the second water sample is conducted, and the second selectively-permeable wall being in contact with the second water sample in the fourth conduit;
continuously directing the second processing liquid continuously through the third conduit while continuously moving the second water sample and the second processing liquid relative to each other while being separated from one another via the second selectively-permeable wall, to generate a second at least partially equilibrated processing liquid and a second processed sample; and
measuring the concentration of the second pre-selected dissolved analyte in a homogenous portion of either the second at least partially equilibrated processing liquid and the second processed sample, wherein the second processing liquid and the second water sample are moved continuously through the second processing cell during measurement.

18. The method of claim 14 wherein the first sample water is configured to be obtained continuously from the quantity of water.

19. The method of claim 14 wherein the at least one detector uses spectrophotometric measurement, utilizing a flow-through optical cell.

20. The method of claim 14 further comprising selecting a device for measuring pH of the first sample water and measuring pH of the first sample water while measuring the concentration of the at least one pre-selected dissolved analyte.

21. The method of claim 14 wherein the method is configured to be performed on at least one of an Autonomous Underwater Vehicle, a Remotely Operated Vehicle, a mobile surface platform, a mobile underwater platform, a stationary surface platform, and a stationary underwater platform.

22. The method of claim 14 wherein the at least one pre-selected analyte is selected from at least one of dissolved inorganic carbon, carbon dioxide, oxygen, ammonia, dissolved nitrogen gas, total alkalinity, and a dissolved metal ion.

* * * * *